US007951613B2

(12) United States Patent
Johnson et al.

(10) Patent No.: US 7,951,613 B2
(45) Date of Patent: May 31, 2011

(54) CHAPERONIN 10 MODULATION OF TOLL-LIKE RECEPTOR-INDUCIBLE CYTOKINE AND CHEMOKINE SECRETION

(75) Inventors: Barbara Jane Johnson, Shailer Park QLD (AU); Andreas Suhrbier, Bunya QLD (AU); Dean Jason Naylor, East Brisbane QLD (AU); Caroline Amanda Dobbin, Holland Park QLD (AU); Christopher Bruce Howard, Rochedale South QLD (AU)

(73) Assignee: CBIO Limited, Eight Mile Plains, Queensland (AU)

( * ) Notice: Subject to any disclaimer, the term of this patent is extended or adjusted under 35 U.S.C. 154(b) by 0 days.

(21) Appl. No.: 12/553,765

(22) Filed: Sep. 3, 2009

(65) Prior Publication Data

US 2009/0325882 A1 Dec. 31, 2009

Related U.S. Application Data

(63) Continuation of application No. 10/586,143, filed as application No. PCT/AU2005/000041 on Jan. 14, 2005, now abandoned.

(30) Foreign Application Priority Data

Jan. 16, 2004 (AU) ................................ 2004900190
Jul. 16, 2004 (AU) ................................ 2004903914

(51) Int. Cl.
*G01N 33/566* (2006.01)
*G01N 33/53* (2006.01)
*A01N 1/02* (2006.01)

(52) U.S. Cl. .............................. 436/501; 435/7.1; 435/2
(58) Field of Classification Search ........................ None
See application file for complete search history.

(56) References Cited

U.S. PATENT DOCUMENTS

2005/0208470 A1 * 9/2005 Latz et al. .......................... 435/4

FOREIGN PATENT DOCUMENTS

| WO | WO 95/15338 A1 | 6/1995 |
| WO | WO 02/40038 A2 | 5/2002 |
| WO | WO 2004/041300 A1 | 5/2004 |
| WO | WO 2004/041304 A2 | 5/2004 |

OTHER PUBLICATIONS

Johnson et al. 2005. J. Biological Chem. 280:4037-4047.*
Harness, J. et al. 2003 "A protective effect of early pregnancy factor on experimental autoimmune encephalomyelitis induced in Lewis rats by inoculation with myelin basic protein", *Journal of the Neurological Sciences* 216: 33-41.
Heldwein, K. A. et al. 2002 "The Role of Toll-Like Receptors in Immunity Against Mycobacterial Infection" *Microbes and Infection* 4:937-944.
Huang, B. et al. 2008 "TLR Signaling by Tumor and Immune Cells: A Double-Edge Sword" *Oncogene* 27:218-224.
Morton, H. et al. 2000 "Production of a recombinant form of early pregnancy factor that can prolong allogeneic skin graft survival time in rats" *Immunology and Cell Biology* 78: 603-607.
Ragno, S. et al. 1996 "A synthetic 10-kD heat shock protein (hsp 10) from *Mycobacterium tuberculosis* modulates adjuvant arthritis" *Clinical and Experimental Immunology* 103: 384-390.
Retzlaff, C. et al. 1994 "Bacterial Heat Shock Proteins Directly Induce Cytokine mRNA and Interleukin-1 Secretion in Macrophage Cultures" *Infection and Immunity* 62: 5689-5693.
Takeda, K. et al. 2003 "Toll-Like Receptors" *Ann Rev Immunol* 21:335-376.
Zhang, B. et al. 2000 "Early pregnancy factor suppresses experimental autoimmune encephalomyelitis induced in Lewis rats with myelin basic protein and in SJL/J mice with myelin proteolipid protein peptide 139-151" *Journal of the Neurological Sciences* 182: 5-15.
Zhang, B. et al. 2003 "Early pregnancy factor treatment suppresses the inflammatory response and adhesion molecule expression in the spinal cord of SJL/J mice with experimental autoimmune encephalomyelitis and the delayed-type hypersensitivity reaction to trinitrochlorobenzene in normal BALB/c mice" *Journal of the Neurological Sciences* 212: 37-46.

* cited by examiner

*Primary Examiner* — Shulamith H Shafer
(74) *Attorney, Agent, or Firm* — Knobbe Martens Olson & Bear LLP

(57) ABSTRACT

Methods of use of Chaperonin 10 (Cpn10) are provided for regulating Toll-like receptor signaling and/or Toll-like receptor inducible immunomodulator secretion. Cpn10 negatively regulates Toll-like receptor agonist-induced pro-inflammatory cytokine and chemokine secretion, examples being IL-6 and RANTES, respectively. Cpn10 positively regulates Toll-like receptor agonist-induced anti-inflammatory cytokine and chemokine secretion, an example being IL-10. These immunoregulatory activities of Cpn10 may be useful in the treatment of diseases, disorders and conditions resulting from excessive pro-inflammatory cytokine and chemokine secretion. This invention also relates to producing, designing and/or screening Cpn10 agonists and antagonists according to their ability to regulate Toll-like receptor signaling and/or Toll-like receptor inducible immunomodulator secretion.

2 Claims, 12 Drawing Sheets

CHAPERONIN 10 MODULATION OF TOLL-LIKE RECEPTOR-INDUCIBLE CYTOKINE AND CHEMOKINE SECRETION

RELATED APPLICATIONS

This application is a continuation of Application No. 10/586,143, filed May 22, 2007, now abandoned, which is United States National Phase under 35 U.S.C. §371 of International Application PCT/AU2005/000041, filed Jan. 14, 2005 designating the U.S., and published in English as WO 2005/067959 on Jul. 28, 2005, which claims priority to Australian Patent Application No. 2004900190, filed Jan. 16, 2004 and Australian Patent Application No. 2004903914, filed Jul. 16, 2004.

BACKGROUND OF THE INVENTION

1. Field of the Invention

This invention relates to use of Chaperonin 10 for modulating Toll-like receptor signaling and/or Toll-like receptor inducible immunomodulator production and/or secretion. More particularly, this invention relates to modulation of Toll-like receptor inducible cytokine and chemokine secretion for treatment of diseases, disorders and conditions resulting from excessive immunomodulator secretion. This invention also relates to producing, designing and/or screening agonists and antagonists of Chaperonin 10.

2. Description of the Related Art

The Toll-like receptor family plays an important role in inflammation and immunity in insects, animals and plants. Toll-like receptors (TLRs) are expressed by cells of the mononuclear lineage including lymphocytes, macrophages and dendritic cells.

TLR2 is activated by TLR2 agonists such as lipoteichoic acid and lipopeptides, which can be components of the outer wall of certain bacteria. TLR3 is activated by agonists such as double stranded RNA derived from viruses.

TLR4 is activated by lipoproteins or lipopolysaccharide (LPS) or endotoxin, which is a component of the outer wall of gram-negative bacteria.

TLR activation by pathogens, or by molecules derived therefrom, induces intracellular signaling that primarily results in activation of the transcription factor NF-κB (Beg, 2002, Trends Immunol. 2002 23 509-12) and modulation of cytokine production. However, a series of other pathways can also be triggered, including p38 mitogen activated kinase, c-Jun-N-terminal kinase and extracellular signal related kinase pathways (Flohe, et al., 2003, J Immunol, 170 2340-2348; Triantafilou & Triantafilou, 2002, Trends Immunol, 23 301-304). The patterns of gene expression induced by ligation of the different TLRs are distinct but often overlap. For instance a large proportion of the genes upregulated by TLR3 agonists and double stranded RNA are also upregulated by TLR4 agonists and LPS (Doyle et al., 2002, Immunity, 17 251-263). TLR4 activation by LPS in macrophages results in TNF-α, IL-12, IL-1β, RANTES and MIP1β secretion (Flohe et al., supra; Jones et al., 2002, J Leukoc Biol, 69 1036-1044).

Mammalian chaperonin 10 (also known as heat shock protein 10) was first described as a mitochondrial protein involved in protein folding, and is a homologue of the bacterial protein GroES. GroES and chaperonin 10 (Cpn10) oligomerise into seven member rings that bind as a lid onto a cup-like structure that comprises seven GroEL or Hsp60 molecules, which tether denatured proteins to the complex (Bukau & Horwich, 1998, Cell, 92 351-366; Hartl & Hayer-Hartl, 2002, Science, 295 1852-1858). Cpn10 is also frequently found at the cell surface (Belles et al., 1999, Infect Immun, 67 4191-4200; Feng et al., 2001, Blood, 97 3505-3512) and in the extracellular fluid (Michael et al., 2003, J Biol Chem, 278 7607-7616; Johnson et al., 2003, Cir Rev Immunol, 23 15-44).

Cpn10 has also been shown to be a suppressive factor present early in pregnancy and has shown immunosuppressive activity in experimental autoimmune encephalomyelitis, delayed type hypersensitivity and allograft rejection models (Zhang et al., 2003, J Neurol Sci, 212 37-46; Morton et al., 2000, Immunol Cell Biol, 78 603-607).

A recent study using *Mycobacterium tuberculosis* Cpn10 described in International Publication WO 02/40038, suggests that this molecule may have efficacy in treating disorders such as cancer, allergic reactions and/or conditions mediated by Th2-type immune responses. It is proposed that this may be achieved through induction of cytokines such as TNF-α and IL-6.

However, the mechanism of action by which Cpn10, and in particular mammalian Cpn10, exerts its immunoregulatory effects has remained obscure.

SUMMARY OF THE INVENTION

Surprisingly, the inventors have demonstrated that Cpn10 regulates Toll-like receptor agonist-mediated stimulation of immunomodulator secretion.

More particularly, Cpn10 down-regulates Toll-like receptor mediated induction of pro-inflammatory immunomodulators and positively regulates Toll-like receptor mediated induction of anti-inflammatory immunomodulator secretion.

Thus, the invention in one broad form is directed to the modulation of Toll-like receptor signaling by chaperonin 10 (Cpn10).

In a first aspect, the invention provides a method of regulating Toll-like receptor signaling in an animal, or in one or more cells, or tissues or organs derived therefrom, including the step of administering Cpn10, or a derivative of Cpn10, to the animal, cells, tissues or organs, to thereby regulate Toll-like receptor signaling.

In a second aspect, the invention provides a method of regulating immunomodulator secretion in an animal, or in one or more cells, or tissues or organs derived therefrom, including the step of administering Cpn10, or a derivative of Cpn10, to the animal, cells, tissues or organs, to thereby regulate Toll-like receptor-inducible immunomodulator production and/or secretion.

According to these aspects, the invention provides a method of regulating Toll-like receptor signaling and/or immunomodulator production and/or secretion to thereby modulate the immune response in an animal to prophylactically or therapeutically treat a disease, disorder or condition.

Preferably, the disease, disorder or condition is selected from acute or chronic inflammatory diseases such as septic shock, inflammatory bowel disease, arthritis, psoriasis, heart disease, atherosclerosis, chronic pulmonary disease, cachexia, multiple sclerosis, GVHD, transplantation and cancer.

According to the invention, Cpn10 preferably regulates a Toll-like receptor selected from the group consisting of TLR2, TLR3 and TLR4.

More preferably, the Toll receptor is selected from the group consisting of TLR2 and TLR4.

Even more preferably, the Toll-like receptor is TLR4.

Suitably, Cpn10 regulates Toll-like receptor signalling and immunomodulator production and/or secretion that is stimulated, activated or induced by a Toll-like receptor agonist.

The Toll-like receptor agonist may be a pathogen, a molecule derived from or produced by a pathogen, or may be a synthetic Toll-like receptor agonist.

Preferably, the Toll-like receptor agonist is selected from the group consisting of LPS, lipopeptide and double-stranded RNA.

In one embodiment, where the Toll-like receptor is TLR4, the agonist is preferably LPS.

In another embodiment, where the Toll-like receptor is TLR3, the agonist is preferably double-stranded RNA.

In yet another embodiment, where the Toll-like receptor is TLR2, the agonist is preferably a lipopeptide.

In particular embodiments, the lipopeptide may be $PAM_3CysSK_4$.

Suitably, the animal or cells, tissues or organs derived therefrom comprise cells that express one or more Toll-like receptors.

Preferably, the cell is an immune cell.

More preferably, the immune cell is a monocyte, macrophage, dendritic cell, or a lymphocyte.

Preferably, the animal is a mammal.

More preferably, the animal is a human.

According to the aforementioned aspects, in one embodiment, the immunomodulator is a pro-inflammatory cytokine, such as TNF-α or interleukin 6 (IL-6), or a pro-inflammatory chemokine, such as RANTES, although without limitation thereto.

In another embodiment, the immunomodulator is an anti-inflammatory cytokine, such as interleukin-10 (IL-10), or anti-inflammatory chemokine, such as TGF-β, although without limitation thereto.

In embodiments where the immunomodulator is a pro-inflammatory cytokine or chemokine, administration of Cpn10 preferably inhibits, suppresses or otherwise reduces production and/or secretion of said immunomodulator.

In embodiments where the immunomodulator is an anti-inflammatory cytokine or chemokine, administration of Cpn10 preferably augments, facilitates, promotes or otherwise increases production and/or secretion of said immunomodulator.

In a third aspect, the invention provides an isolated molecular complex comprising a Toll-like receptor, a Toll-like receptor agonist and Cpn10.

Preferably, the Toll-like receptor is selected from the group consisting of TLR2, TLR3 and TLR4.

More preferably, the Toll receptor is selected from the group consisting of TLR2 and TLR4.

Even more preferably, the Toll-like receptor is TLR4.

In one embodiment, where the Toll-like receptor is TLR4, the agonist is LPS.

In another embodiment, where the Toll-like receptor is TLR3, the agonist is double-stranded RNA.

In yet another embodiment, where the Toll-like receptor is TLR2, the agonist is $PAM_3CysSK_4$.

In one particular embodiment, the invention provides an isolated molecular complex comprising TLR4, LPS and Cpn10.

In a fourth aspect, the invention provides a method of producing, designing or screening a Cpn10 agonist, including the step of determining whether a candidate agonist mimics or augments Cpn10 regulation of Toll-like receptor signaling and/or Toll-like receptor-inducible immunomodulator production and/or secretion.

In a fifth aspect, the invention provides a method of producing, designing or screening a Cpn10 antagonist, including the step of determining whether a candidate antagonist inhibits, reduces, suppresses or otherwise decreases Cpn10 regulation of Toll-like receptor signaling and/or Toll-like receptor-inducible immunomodulator production and/or secretion.

Preferably, the Toll-like receptor is selected from the group consisting of TLR2, TLR3 and TLR4.

More preferably, the Toll receptor is selected from the group consisting of TLR2 and TLR4.

Even more preferably, the Toll-like receptor is TLR4.

In a sixth aspect, the invention provides a Cpn10 agonist or antagonist produced, designed or screened according to the aforementioned aspects.

Throughout this specification, "comprise", "comprises" and "comprising" are used inclusively rather than exclusively, will be understood to imply the inclusion of a stated integer or group of integers but not the exclusion of any other integer or group of integers.

DETAILED DESCRIPTION OF THE PREFERRED EMBODIMENT

Figure 1:
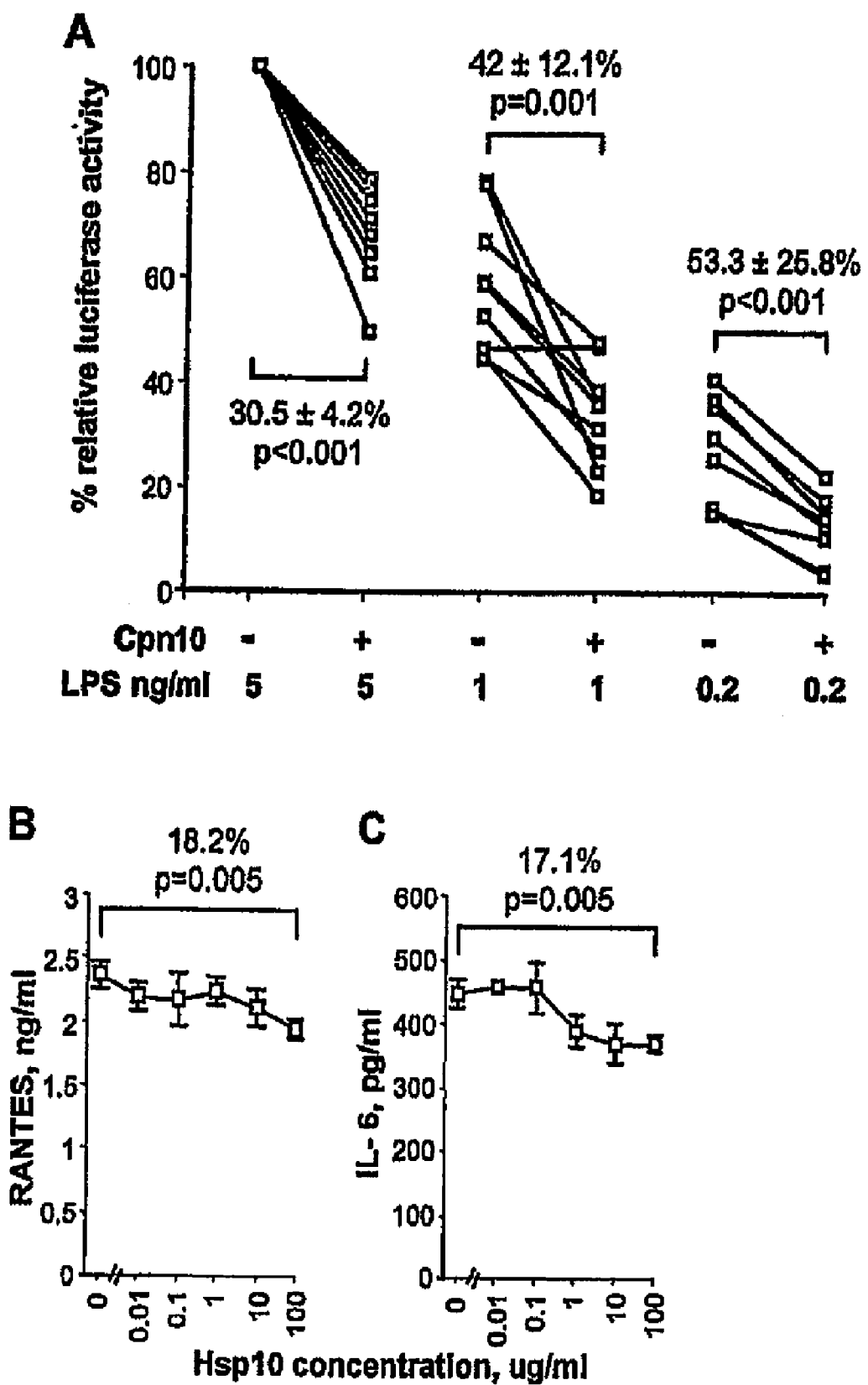
FIG. 1. Cpn10 inhibits LPS-induced activation of RAW264.7 cells and pro-inflammatory mediator production. (A) Cpn10-mediated inhibition of LPS-induced NF-κB activity. In 9 separate experiments 100 μg/ml of Cpn10 (Hsp10+) or buffer (Hsp10−) was preincubated with RAW264-HIV-LTR-LUC cells for 2 h. LPS was then added at 5, 1 and 0.2 ng/ml and luciferase activity measured 2 h later. The relative light units (RLU) of luciferase obtained for 5 ng/ml of LPS was set at 100% relative luciferase activity, and 0% represents the RLU obtained in the absence of LPS. Cpn10 alone did not stimulate significant RLU (data not shown). The mean percentage reduction (±SD) in RLU mediated by Cpn10 is indicated for each concentration of LPS, and the significance calculated using a paired t test. (B, C) Cpn10-mediated inhibition of LPS-induced RANTES and IL-6 secretion. RAW264.7 cells were incubated with the indicated Cpn10 (Hsp10) concentration for 2 h followed by the addition of 1 ng/ml of LPS. After 6 h, triplicate supernates were analysed for RANTES and IL-6 by ELISA. The mean percentage reduction in RANTES and IL-6 secretion mediated by 100 μg/ml Cpn10 is indicated. Significance was calculated using a paired t test.

The present invention has arisen, at least in part, from the discovery that, in a number of different human and murine in vitro and in vivo systems, Cpn10 inhibits LPS-mediated secretion of the pro-inflammatory cytokines TNF-α and IL-6 and the pro-inflammatory chemokine RANTES, and increases LPS-induced secretion of the anti-inflammatory cytokine IL-10 in cells including monocytes, macrophages and mononuclear cells.

This is in contrast to International Publication WO 02/40038 which proposes that mycobacterial Cpn10 acts to suppress Th2-mediated immune responses, by increasing expression of cytokines such as TNF-α and IL-6.

Although not wishing to be bound by any particular theory, according to the present invention, Cpn10 acts neither via a Th1- nor a Th2-dependent mechanism.

The inventors have unexpectedly demonstrated that Cpn10 affects Toll-like receptor signaling and resultant immunomodulator secretion in response to Toll-like receptor agonists.

More particularly, Cpn10 reduces Toll-like receptor agonist-stimulated NF-κB activation, and TNF-α and RANTES secretion, and increases IL-10 secretion in a dose-dependent manner.

Furthermore, the inventors have also demonstrated that Cpn10, Toll-like receptors and Toll-like receptor agonists form a molecular complex. FRET analysis suggests that there may be a direct interaction between Cpn10 and Toll-like receptor, or that at least they are in very close spatial proximity (within 1-10 nm of each other), in the presence of TLR ligand (e.g., LPS).

It will be appreciated that a Toll-like receptor agonist may be a pathogen (such as a bacterium or a virus), a molecule derived from, or produced by, a pathogen (such as bacterial LPS, bacterial endotoxin, mycobacterial lipoarabinomannan, lipoteichoic acid, a lipopeptide or viral double stranded RNA), or may be a synthetic lipopeptide Toll-like receptor agonist such as peptide/amino acid linked to long-chain acylated saturated fatty acids such as lauric or palmitic acid, for example the TLR2 agonist PAM$_3$CysSK$_4$.

For the purposes of the invention, by "immunomodulators" is meant a molecular mediator secreted by cells of the immune system or a molecular mediator which interacts with cells of the immune system that plays a role in activation, maintenance, maturation, inhibition, suppression or augmentation of an immune response.

By "cytokine" is meant a molecular mediator secreted by cells of the immune system that plays a role in activation, maintenance, maturation, inhibition, suppression or augmentation of an immune response. Non-limiting examples of cytokines are TNF-α, interleukin-6 (IL-6), interleukin-12 (IL-12), interleukin -1β (IL-1β) and interleukin-10 (IL-10).

By "chemokine" is meant a molecular mediator that acts to promote and/or regulate cell migration and activation. Non-limiting examples of a chemokines are MIP 1α, MIP 1β, RANTES and TGF-β.

By "pro-inflammatory immunomodulators" is meant a cytokine or chemokine that plays a role or has some involvement in an inflammatory process or inflammatory response.

Non-limiting examples of pro-inflammatory immunomodulators are IL-6, TNF-α, IL-12 and IL-1β, RANTES and MIP1β.

By "anti-inflammatory immunomodulators" is meant a cytokine or chemokine that plays a role in inhibiting, suppressing or otherwise decreasing an inflammatory response.

Non-limiting examples of anti-inflammatory immunomodulators are IL-10 and TGF-β.

By "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

By "protein" is meant an amino acid polymer. The amino acids may be natural or non-natural amino acids D- and L-amino acids, as are well understood in the art.

A "peptide" is a protein having no more than fifty (50) amino acids.

A "polypeptide" is a protein having more than fifty (50) amino acids.

The term "nucleic acid" as used herein designates single- or double-stranded mRNA, RNA, RNAi and DNA inclusive of cDNA and genomic DNA.

Cpn10 and Cpn10 Fragments, Variants and Derivatives

According to the present invention, "Cpn10" or "chaperonin 10" refers to any eukaryotic Cpn10, including mammalian Cpn10 such as human, mouse, rat and other forms of Cpn10.

Preferably, Cpn10 is mammalian Cpn10.

More preferably, Cpn10 is human Cpn10.

Cpn10 protein may comprise naturally occurring modification such as glycosylation or acetylation and/or be in native, chemical synthetic or recombinant form. It will also be appreciated that Cpn10 may be referred to as "Hsp10". These are to be treated as referring to the same protein.

According to the invention, fragments of Cpn10 may also be used.

In one embodiment, a "fragment" includes an amino acid sequence that constitutes less than 100%, but at least 30%, preferably at least 50%, more preferably at least 80% or even more preferably at least 90%, 95% or 98% of a Cpn10 protein.

The term "fragment" includes and encompasses a "biologically active fragment", which retains a biological activity of a Cpn10 protein. For example, a biologically active fragment of Cpn10 capable of regulating Toll-like receptor signaling and/or immunomodulator secretion may be used in accordance with the invention. The biologically active fragment constitutes at least greater than 50% of the biological activity of the entire Cpn10 protein, preferably at least greater than 60% biological activity, more preferably at least greater than 75% biological activity, even more preferably at least greater than 80% biological activity and advantageously at least 90% or 95% of a biological activity of Cpn10.

As used herein, "variant" proteins are proteins in which one or more amino acids have been replaced by different amino acids. Protein variants of Cpn10 that retain biological activity of native or wild type Cpn10 may be used in accordance with the invention. It is well understood in the art that some amino acids may be changed to others with broadly similar properties without changing the nature of the activity of the protein (conservative substitutions). Generally, the substitutions which are likely to produce the greatest changes in a polypeptide's properties are those in which (a) a hydrophilic residue (e.g., Ser or Thr) is substituted for, or by, a hydrophobic residue (e.g. Leu, Ile, Phe or Val); (b) a cystine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

With regard to Cpn10 variants, these can be created by mutagenising a Cpn10 protein or by mutagenising an encoding nucleic acid, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al., supra which is incorporated herein by reference.

As used herein, "derivative" Cpn10 proteins of the invention include Cpn10 proteins, which have been altered, for example by conjugation or complexing with other chemical moieties or by post-translational modification techniques as would be understood in the art, inclusive of fusion partner proteins.

Other derivatives contemplated by the invention include, but are not limited to, pegylation, modification to side chains, incorporation of unnatural amino acids and/or their derivatives during protein synthesis and the use of crosslinkers and other methods which impose conformational constraints on Cpn10 protein. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulfhydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

Derivatives may also include fusion partners and epitope tags. Well known examples of fusion partners include, but are not limited to, glutathione-S-transferase (GST), Fc portion of human IgG, maltose binding protein (MBP) and hexahistidine ($HIS_6$), which are particularly useful for isolation of the fusion protein by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

One particular example of a fusion partner is GST, such as described in Morton et al., 2000, Immunol Cell Biol 78 603-607. In some cases, the fusion partners also have protease cleavage sites, such as for Factor $X_a$ or Thrombin, which allow the relevant protease to partially digest the fusion polypeptide of the invention and thereby liberate the recombinant Cpn10 protein therefrom. The liberated Cpn10 protein can then be isolated from the fusion partner by subsequent chromatographic separation. Upon cleavage of GST-Cpn10 with thrombin, the derivative GSM-Cpn10 protein is produced, for example.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Cpn10 proteins according to the invention (inclusive of fragments, variants, derivatives and homologues) may be prepared by any suitable procedure known to those of skill in the art, including chemical synthesis and recombinant expression.

Preferably, Cpn10 is recombinant Cpn10.

For example, the recombinant Cpn10 protein may be prepared by a procedure including the steps of:

(i) preparing an expression construct which comprises an isolated nucleic acid encoding Cpn10, operably-linked to one or more regulatory nucleotide sequences in an expression vector;

(ii) transfecting or transforming a suitable host cell with the expression construct; and (iii) expressing the recombinant protein in said host cell.

The method described in Morton et al., 2000, supra is an example of a recombinant Cpn10 protein production method.

Methods of Treatment and Pharmaceutical Compositions

The present invention provides methods whereby Cpn10-mediated regulation of Toll-like receptor signalling and, more particularly, immunomodulator secretion, may be used to prophylactically or therapeutically treat responsive diseases, disorders or conditions.

Such diseases, disorders or conditions may be caused by excessive levels of pro-inflammatory cytokines and chemokines, and thus be responsive to inhibiting, suppressing or otherwise reducing Toll-like receptor signaling.

Alternatively or additionally, such diseases, disorders or conditions may be responsive to augmenting, facilitating, promoting or otherwise increasing Toll-like receptor signaling and anti-inflammatory cytokine and chemokine secretion.

For example, Cpn10 reduces TNF-α and RANTES production and increases IL-10 production in an in vivo non-lethal endotoxemia model in mice. Cpn10 also has significant immunosuppressive activity in an in vivo mouse transplantation model and Cpn10 treatment increases the survival rate of mice suffering from graft versus host disease.

Cpn10 also reduces cachexia in rats suffering from adjuvant-induced arthritis. Elevated levels of inflammatory cytokines are associated with cachexia in a number of diseases, such as cancer and rheumatoid arthritis.

In addition Cpn10 improves wound healing in an in vivo mouse model.

Cpn10 administered as a single intravenous dose to humans in vivo, markedly reduces the pro-inflammatory cytokine response following LPS-stimulation ex vivo in a dose-responsive manner clearly demonstrating that Cpn10 has immunomodulatory effects in human clinical trial subjects.

Excessive inflammation or uncurtailed immune responses are detrimental to a host, hence a number of negative feedback systems have evolved to dampen production of pro-inflammatory mediators. One such negative feedback mechanism includes IL-10, an important immunoregulatory cytokine secreted by mononuclear cells and monocytes, which is involved in limitation of inflammatory responses and induction of immune tolerance.

Cpn10 inhibits but does not abolish TNF-α, IL-6 or RANTES secretion. This is a desirable characteristic since complete TNF-α removal (for example, by anti-TNF -α antibodies) can result in compromised immunity, predisposing patients to infection, and reduced tumour surveillance which may predispose patients to increased frequency of tumours.

The ability of Cpn10 to reduce production and/or secretion of pro-inflammatory immunomodulators indicates that Cpn10 will find therapeutic application in conditions where excessive pro-inflammatory immunomodulator secretion leads to disease.

Many diseases are associated with excessive or chronic inflammation, hence modulation of TLR receptor signaling resulting in modulation of cytokine secretion may have widespread clinical benefits. For example, excessive secretion of pro-inflammatory cytokines, such as TNF-α is one of the leading causes of death in acute conditions such as septic shock, and it is one of the main factors contributing to ongoing tissue damage in chronic inflammatory diseases such as inflammatory bowel disease (IBD), arthritis, psoriasis, congestive heart disease, multiple sclerosis, and chronic obstructive pulmonary disease.

In tissue or organ transplantation the host or donor lymphocytes can recognize the donor or host cell antigens, respectively, as foreign and release cytokines which activate cells of the innate immune system resulting in rejection of the transplanted tissue or organ or graft versus host disease. Immunosuppressive drugs play a large role in the therapeutic treatment and management of transplant rejection and graft versus host disease. However, the drugs evoke severe side effects in patients, they are very expensive and in some patients they are poorly effective.

Cpn10, inclusive of variants, fragments and derivatives of Cpn10, may be administered to an animal in vivo or may be administered in vitro to one or more cells, tissues or organs obtained from an animal to thereby regulate Toll-like receptor signaling and/or Toll-like receptor-inducible immunomodulator production and/or secretion.

Typically, although not exclusively, Cpn10 inclusive of variants, derivatives and fragments may be delivered as a pharmaceutical compositions that further comprises an appropriate pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intramuscular, intra-dermal, subcutaneous, inhalational, intraocular, intraperitoneal, intracerebroventricular, transdermal and the like may be employed. Intra-muscular and subcutaneous injection is appropriate, for example, for administration of immunogenic compositions, vaccines and DNA vaccines.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

The above compositions may be administered in a manner compatible with the dosage formulation, and in such amount as is pharmaceutically-effective. The dose administered to a patient, in the context of the present invention, should be sufficient to affect a beneficial response in a patient over an appropriate period of time. The quantity of agent (s) to be administered may depend on the subject to be treated inclusive of the age, sex, weight and general health condition thereof, factors that will depend on the judgment of the practitioner.

Pharmaceutical compositions and methods of treatment according to the invention may be suitable for medical and/or veterinary use and accordingly practiced on human and non-human animals inclusive of mammals such as humans, livestock, domestic animals and performance animals, although without limitation thereto.

Cpn10 Agonists and Antagonists

The present invention contemplates methods to engineer, design, screen or otherwise produce a Cpn10 agonist or antagonist.

The elucidation of the effect of Cpn10 upon Toll-like receptor signaling and immunomodulator secretion provides a new and unexpected opportunity whereby Cpn10 agonists and antagonists may be specifically designed or screened according to their effect upon Toll-like receptor signaling and immunomodulator secretion. In principle, this immunoregulatory activity may be independent of chaperone activity also possessed by Cpn10.

An "agonist" refers to a molecule which enhances the activity of another molecule or a receptor site.

Typically, a Cpn10 agonist suppresses, reduces or otherwise inhibits pro-inflammatory cytokine or chemokine secretion normally induced by a Toll-like receptor agonist.

Typically, a Cpn10 agonist augments, facilitates or otherwise increases anti-inflammatory cytokine or chemokine secretion normally induced by a Toll-like receptor agonist.

An "antagonist" refers to a molecule which blocks or inhibits the activity of another molecule or a receptor site.

Typically, a Cpn10 antagonist suppresses, reduces or otherwise inhibits the ability of Cpn10 to negatively regulate pro-inflammatory cytokine or chemokine secretion induced by a Toll-like receptor agonist.

Typically, a Cpn10 antagonist inhibits the ability of Cpn10 to positively regulate induction of anti-inflammatory cytokine or chemokine secretion by a Toll-like receptor agonist.

In one embodiment, the agonist or antagonist may be a mimetic of Cpn10, although the invention is not limited to agonists and/or antagonists having structural similarity to Cpn10.

A "mimetic" is used herein to refer to a molecule that resembles one or more particular structural and/or functional regions or domains of Cpn10 and includes modified forms of Cpn10 that have agonist or antagonist activity.

In one particular form, the present invention provides a method whereby Cpn10 agonists and/or antagonists may be engineered, designed, screened or otherwise produced by determining whether a candidate Cpn10 agonist or antagonist regulates Toll-like receptor signaling and/or Toll-like receptor-inducible immunomodulator secretion.

It will be appreciated that according to the invention, Toll-like receptor signaling and immunomodulator production and/or secretion may be measured or detected at the level of gene expression (e.g. production of endogenous cytokine or chemokine RNA), by measuring or detecting intracellular or extracellular, secreted protein, reporter gene assays and assays that detect or measure intracellular signaling molecules.

In one particular embodiment, the invention provides a method whereby Toll-like receptor signaling is measured or detected according to NF-κB activity in vitro.

In another particular embodiment, the invention provides a method whereby Toll-like receptor signaling is measured or detected according to secretion of one or more immunomodulators such as IL-6, TNF-α, RANTES, IL-10, IL-12, and IL-1α production and/or secretion.

In yet another particular embodiment, the invention provides a method whereby Toll-like receptor signaling is measured or detected according to c-Jun-N-terminal kinase and/or extracellular signal related kinase signaling.

According to the invention, an isolated molecular complex comprising Cpn10, a Toll-like receptor and a Toll-like receptor agonist may be used to produce, design or screen a Cpn10 agonist or antagonist.

In a particular form, the isolated molecular complex comprises Cpn10, TLR-4 and LPS.

By way of example only, a candidate agonist may be identified by an ability to form a molecular complex with a Toll-like receptor and a Toll-like receptor agonist.

By way of example only, a candidate antagonist may be identified by an ability to prevent or disrupt formation of a molecular complex comprising Cpn10, a Toll-like receptor and a Toll-like receptor agonist.

In light of the foregoing, it will be appreciated that there are several techniques that may facilitate production of Cpn10 agonists and/or antagonists according to the invention.

Non-limiting examples include screening libraries of molecules such as synthetic chemical libraries, including combinatorial libraries, by methods such as described in Nestler & Liu, 1998, Comb. Chem. High Throughput Screen. 1,113 and Kirkpatrick et al., 1999, Comb. Chem. High Throughput Screen 2 211.

It is also contemplated that libraries of naturally-occurring molecules may be screened by methodology such as reviewed in Kolb, 1998, Prog. Drug. Res. 51 185.

More structural approaches may employ computer assisted screening of structural databases, computer-assisted modeling and/or design, or more traditional biophysical techniques which detect molecular binding interactions, as are well known in the art.

Computer-assisted structural database searching, modeling and design is becoming increasingly utilized as a procedure for engineering agonists and antagonist molecules. Examples of database searching methods may be found in International Publication WO 94/18232 (directed to producing HIV antigen mimics), U.S. Pat. No. 5,752,019 and International Publication WO 97/41526 (directed to identifying EPO mimetics), each of which is incorporated herein by reference.

Generally, other applicable methods include any of a variety of biophysical techniques which identify molecular interactions. Methods applicable to potentially useful techniques such as competitive radioligand binding assays, analytical ultracentrifugation, microcalorimetry, surface plasmon resonance and optical biosensor-based methods are provided in Chapter 20 of CURRENT PROTOCOLS IN PROTEIN SCIENCE Eds. Coligan et al., (John Wiley & Sons, 1997) which is incorporated herein by reference.

So that the present invention may be more readily understood and put into practical effect, the skilled person is referred to the following non-limiting examples.

EXAMPLES

Example 1

Cpn10 Modulation of LPS-stimulated Cytokines and Chemokines

Materials and Methods
Production and Purification of Cpn10

Recombinant human Cpn10 (GenBank accession no. X75821) was produced in *E. coli* essentially as described by Ryan et al. (Ryan et al., 1995, J Biol Chem, 270 22037-22043). In addition, the material that did not bind Macro-Prep High Q (BioRad) was further purified by S-Sepharose and then Gel-Filtration (Superdex 200, Amersham Biosciences). Purified Cpn10 in a 50 mM Tris-HCl (pH 7.6) and 150 mM NaCl buffer, was filtered through an Acrodisc with a 0.2 mm Mustang E membrane according to the manufacturer's instructions (Pall Corporation, Ann Arbor, Mich. Cat No. MSTG5E3) to remove residual endotoxins and was stored at −70° C. The purity of Cpn10 was determined to be >97% by SDS-PAGE. Aliquots were thawed once prior to use. All batches of Cpn10 showed the same molar activity as *E. coli* GroES in GroEL-mediated rhodanese refolding assays (Brinker et al., 2001, Cell, 107 223-233) (data not shown). LPS contamination of Cpn10 was determined by the Limulus Amebocyte Lysate assay (BioWhittaker, Walkersville, Md.) to be <1 EU/mg of purified Cpn10 protein.

Tumour Cell Lines

K562 (human erythroleukemia), Mono Mac 6 (human monocytic line), U937 (human histiocytic lymphoma), P815 (mouse mastocytoma), EL4 (mouse T cell lymphoma), Jurkat (human T cell leukemia), RAW 264.7 (ATCC TIB 71, mouse macrophage), L929 (mouse fibrosarcoma), B16 (mouse melanoma), HeLa (human cervical carcinoma), and MCA-2 (mouse fibrosarcoma) cell lines were shown to be mycoplasma negative. Cells were grown in endotoxin-free medium comprising RPMI 1640 (Gibco Labs, Life Technologies, Grand Island, N.Y., USA), 10% fetal bovine serum (Life Technologies), 2 mM glutamine (Sigma), 10 mM HEPES (Sigma), 100 µg/ml of streptomycin and 100 IU/ml of penicillin (CSL Ltd, Melbourne, Australia).

RAW264-HIV-LTR-LUC Bioassay

RAW264-HIV-LTR-LUC cells were cultured in the presence of G418 (200 µg/ml) for one week after recovery from liquid nitrogen and grown as suspension cultures in 25 cm$^3$ flasks (Greiner Labortechnik, Frickenhausen, Germany). RAW264-HIV-LTR-LUC cells were disaggregated by repeated pipetting and plated at $2.5 \times 10^5$ cells/well in 24-well plates and incubated overnight (37° C. and 5% $CO_2$). LPS from *E. coli* (Sigma L-6529. Strain 055:B5, Sigma) was dissolved in sterile distilled water and stored at 4° C. at 1 mg/ml in glass vials. Immediately prior to use the solution was vigorously vortexed before aliquots were taken. Cpn10 was added to cell cultures for 2 h followed by addition of LPS at the indicated concentrations, and after a further 2 h the adherent cells were processed for the luciferase assay (Luciferase Assay System, Promega, Madison, Wis.). Luciferase activity was read for 15 sec on a Turner Designs Luminometer TD 20/20.

RAW264. 7 IL-6 and RANTES Assays

RAW264.7 cells were seeded at $2.5 \times 10^5$ cells/well in 24-well plates and cultured overnight at 37° C. and 5% $CO_2$. Cpn10 or buffer was added to cells in triplicate for 2 h followed by the addition of LPS (1 ng/ml). After 6 h supernatants were collected and analysed in triplicate for production of RANTES and IL-6 by Duoset ELISA kit (R & D Systems). The optical density (450 nm) of each sample was determined using a microplate reader (Magellan 3, Sunrise-Tecan, Durham, N.C.).

Cytokine Production from Splenocytes and Macrophages Derived from Cpn10 Treated Animals C57BL/6 ($H-2^b$, Ly-5.2$^+$) mice were purchased from the Australian Research Centre (Perth, Western Australia, Australia) and C57BL/6 IL-10$^{-/-}$ mice (H-2b, Ly-5.2$^+$) were supplied by the Australian National University (Canberra, Australia). The culture medium used throughout was 10% FCS/IMDM (JRH Biosciences, Lenexa, Kans.), supplemented with 50 units/ml penicillin, 50 µg/ml streptomycin, 2 mM L-glutamine, 1 mM sodium pyruvate, 0.1 mM non-essential amino acid, 0.02 mM β-mercaptoethanol, and 10 mM HEPES, and cells were cultured at pH 7.75, 37° C. and 5% $CO_2$. C57BL/6 mice (n=3 per group) were treated with subcutaneous injections of Cpn10 (100 µg) or diluent daily for 5 days, peritoneal macrophages were harvested the next day by peritoneal lavage and pooled from individual animals within the treatment group. Cells were plated in triplicate at $2 \times 10^5$/well in the presence of LPS (1 µg/ml). Culture supernatants were collected at 5 h and levels of TNF-α were assessed by ELISA (see below). Results were normalized to production per $10^5$ macrophages based on CD11b staining by FACS analysis of input cells. For IL-10 determination splenocytes were harvested from the same animals and pooled as above and cultured in triplicate at $5 \times 10^5$/well in the absence (not shown) or presence of LPS (10 µg/ml). Culture supernatants were collected at 48 h and levels of IL-10 determined by ELISA (see below).

Cytokine Assays for Murine Cells Stimulated In Vitro with LPS

The monoclonal antibody pairs used in the TNF-α and IL-10 ELISA assays were purchased from PharMingen (San Diego, Calif.) and used at concentrations recommended by the manufacturer. Supernatants were diluted in culture medium 1:1 IL-10 and TNF-α. Cytokines were captured by the capture antibody, and detected by the direct biotin-labelled detection antibody. Strepavidin-labelled horse-radish peroxidase (Kirkegaard and Perry laboratories, Gaithersburg, Md.) and substrate (Sigmafast OPD) was then used to measure immobilized biotin. Plates were read at 492 nm using the Spectraflour Plus microplate reader (Tecan). Recombinant cytokines (PharMingen) were used as standards for ELISA assays. Standards were run in duplicate and the sensitivity of the assays was 15 pg/ml for IL-10 and TNF-α.

Human PBMC TNF-α and IL-6 Assays

Human peripheral blood mononuclear cells (PBMCs) were isolated from heparinized blood from healthy volunteers by buoyant density gradient centrifugation on Ficoll-Hypaque. PBMCs were dispensed at $10^6$ viable cells/ml in 200 µl in 96-well tissue culture plates (Greiner). Cpn10 was then added and plates were incubated for 1 h, followed by LPS addition and a further 20 h incubation at 37° C., 5% $CO_2$, after which supernatants were collected and duplicate samples analysed for TNF-α and IL-6 production (Duoset ELISA kits; R & D Systems). The sensitivity of these assays was 31 pg/ml TNF-α and 9 pg/ml IL-6.

Mouse Serum TNF-αa, RANTES and IL-10 Assays after LPS Injection

Female 8-10 week old BALB/c mice (Animal Resource Centre, Perth, Australia) were placed under a heating lamp for approximately 10 minutes, then restrained and Cpn10 injected i.v. at the specified doses. After 30 mins, 10 µg LPS was injected i.v. using the same protocol. At 1.5 hours post LPS injection, blood was collected by heart puncture into 1 ml clotting accelerator tubes (MiniCollect, Interpath) and stored at 4° C. for analysis of serum TNF-α and RANTES using the ELISA kits (R & D Systems). IL-10 production in serum was measured with mouse OptEIA IL-10 specific ELISA (BD Biosciences Pharmingen).

Bone Marrow Trafasplantation and Graft Versus Host Disease (GVHD)

Female 8-14 week old C57BL/6 (B6, $H-2^b$, Ly-5.2$^+$), B6 Ptprc$^a$ Ly 5$^a$ ($H-2^b$, Ly-5.1$^+$) and B6D2F1 ($H-2^{b/d}$, Ly-5.2$^+$) mice were purchased from the Australian Research Centre (Perth, Western Australia, Australia). Cpn10 (100 µg per animal) or control diluent was injected subcutaneously daily for 5 days into donor and recipient animals prior to transplant. Mice were housed in sterilized microisolator cages and received acidified autoclaved water (pH 2.5) and normal food for the first two weeks post-transplantation. Mice were transplanted according to a standard protocol described previously (Hill et al., 1997, Blood, 90 3204-3213; Hill et al., 1998, J Clin Invest, 102, 115-123). Briefly, on day 1, B6D2F1 mice received 1300 cGy total body irradiation ($^{137}$Cs source at 108 cGy/min), split into two doses separated by 3 h to minimise gastrointestinal toxicity. Donor bone marrow ($5 \times 10^6$) and donor nylon wool purified splenic T cells ($2 \times 10^6$) were resuspended in 0.25 ml of Leibovitz's L-15 media (Gibco BRL, Gaithersburg Md.) and were injected intravenously into each recipient. Survival was monitored daily, and GVHD clinical scores measured weekly. The degree of systemic GVHD was assessed by a scoring system which sums changes in five clinical parameters; weight loss, posture (hunching), activity, fur texture and skin integrity (maximum index=10) (Hill et al., 1997, supra; Hill et al., 1998, J Clin Invest, 102 115-123; Cook et al., 1996, Blood, 88 3230-3239). Individual mice were ear-tagged and graded from 0 to 2 for each criterion without knowledge of treatment group. Animals with severe clinical GVHD (scores >6) were sacrificed according to ethical guidelines and the day of death deemed to be the following day.

Statistical Analysis

Statistical analysis was performed using univariate analysis of variance (ANOVA), Student's t test or log rank statistic using SPSS for Windows 11.5.0 (SPSS Inc.).

Results

Inhibition of LPS Signaling by Cpn10 Using RAW264-HIV-LTR-LUC indicator cells

To investigate the role of Cpn10 as an immunosuppressive agent the ability of Cpn10 to inhibit LPS-mediated NF-κB activation was investigated. The RAW264-HIV-LTR-LUC cells are a mouse macrophage cell line (RAW264.7) stably expressing a luciferase reporter gene with an HIV long terminal repeat promoter, which is highly and rapidly responsive to NF-κB stimulation. These cells provide a sensitive bioassay for analysis of TLR4 signaling pathways in macrophages stimulated with bacterial LPS (Sweet & Hume, 1995, J Inflamm, 45 126-135). To avoid the use of supra-physiological levels of LPS, a titration range for LPS concentration was established, which represented approximately 80%, 50% and 20% of maximal LPS-stimulated luciferase activity (5, 1 and 0.2 ng, respectively) (data not shown). Preincubation of the reporter cells with 100 μg/ml of Cpn10 for 2 hours was able to inhibit significantly LPS-stimulated luciferase activity by 30-50% at these concentrations of LPS (FIG. 1A). Shorter preincubation times provided less reproducible inhibition and preincubation times above 18 hours provided no inhibition (data not shown).

Cpn10-mediated Inhibition of IL-6 and RANTES Production in LPS-stimulated RAW264. 7 cells To illustrate that Cpn10-mediated inhibition of LPS-induced NF-κB activation translated to reduction in the secretion of pro-inflammatory mediators, the ability of Cpn10 to inhibit LPS-induced production of the pro-inflammatory cytokine IL-6 and the pro-inflammatory chemokine RANTES was investigated. An LPS dose of 1 ng was used, which induced approximately 50% of maximal RANTES production in this assay (data not shown). The 2 h preincubation period (similar to that used above) was unable to induce tolerance in these assays irrespective of the dose of LPS used (data not shown). Cpn10 mediated a dose related reduction in both LPS-induced RANTES (FIG. 1B) and IL-6 (FIG. 1C) secretion, illustrating that inhibition of NF-κB activation in this system leads to reduction in pro-inflammatory mediator secretion.

Cpn10-mediated Inhibition of LPS-induced TNF-α was Independent of IL-10

To determine the effect of Cpn10 in a more physiological cell population, mice were treated with Cpn10 and their peritoneal macrophages removed and stimulated with LPS in vitro. The Cpn10 treatment significantly reduced the LPS-induced secretion of TNF-α from these cells (FIG. 2A), illustrating that Cpn10 mediates similar effects on macrophages treated in vivo as seen with RAW264.7 cells treated in vitro.

Figure 2:
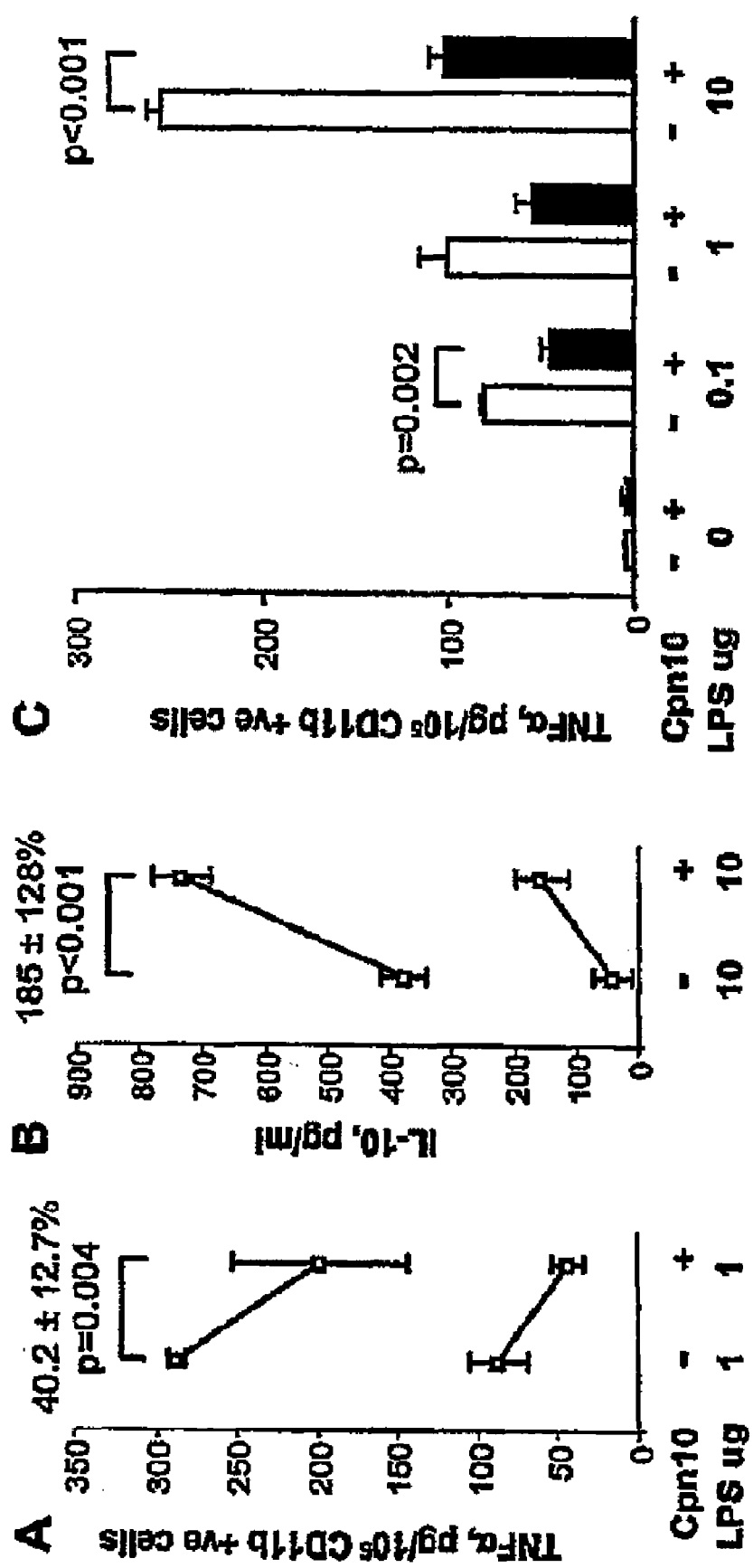
FIG. 2. Effect of Cpn10 on cytokine secretion in murine systems. (A) Cpn10 treatment reduced capacity of LPS-stimulated peritoneal macrophages to produce TNF-α. C57BL/6 mice (n=3) were treated with Cpn10 (Cpn10+) or control diluent (Cpn10−). Peritoneal macrophages were harvested by peritoneal lavage on day 6 and pooled from individual animals within the treatment group. Cells were plated at $2 \times 10^5$/well in the presence of LPS (1 μg/ml). Culture supernatants were collected at 5 hours and levels of TNF-α were assessed by ELISA. (Wells without LPS produced no detectable TNF-α-data not shown). Mean SE of triplicate wells are shown, and are normalized to production per $10^5$ macrophages based on CD11b staining. Data from two identical experiments are shown and the average percentage reduction is indicated with the significance calculated by ANOVA. (B) Cpn10 treatment augmented IL-10 production from splenocytes. C57BL/6 mice were treated with either Cpn10 or control diluent as above. Splenocytes were harvested on day 6 and pooled from individual animals within a treatment group and cultured at $5 \times 10^5$/well in the presence of LPS (10 μg/ml). Culture supernatants were collected at 48 hours and levels of IL-10 determined by ELISA. Means±SE of triplicate wells are shown. Average percentage increase is shown with statistics calculated as for A. (C) Cpn10 treatment reduced TNF-α production from IL-10$^{-/-}$ peritoneal macrophages. IL-10$^{-/-}$ C57BL/6 mice were treated with Cpn10 or control diluent as above and peritoneal macrophages were harvested as for A. After 5 hours of culture in the presence of LPS (0.1, 1 or 10 μg/ml) TNF-α was determined in culture supernatants by ELISA. Mean±SE of triplicate wells for one representative experiment is shown. TNF-α levels were compared for Cpn10 treated and control animals using a non-parametric t test.

IL-10 is a potent immunosuppressive cytokine able to inhibit TLR4 signaling (Berlato et al., 2002, J Immunol, 168 6404-6411; Suhrbier & Linn, 2003, Trends Immunol, 24 165-168), and when splenocytes from Cpn10 treated animals were stimulated with LPS, significantly increased IL-10 production was observed compared to control animals (FIG. 2B). However, the Cpn10-mediated reduction in LPS-induced TNF-α production (FIG. 2A) did not require IL-10, since similar reductions in TNF-α secretion were observed when peritoneal macrophages from Cpn10 treated IL-10−/− mice were stimulated with LPS in vitro (FIG. 2C). Thus, reduced TNF-α secretion and increased IL-10 production appear to be independent consequences of Cpn10 treatment.

Cph10-treatment of Human Peripheral Blood Mononuclear Cells (PBMC)

To determine whether Cpn10 is also active on primary human cells, PBMC from healthy donors were pretreated with Cpn10 or buffer for 1 h and then stimulated with 0.04 ng/ml LPS for 20 h. This dose of LPS was established as the lowest dose reliably able to stimulate significant TNF-α secretion (Johnson et al., 2004, J Biol Chem, in press) and corresponds to the dose in humans that produces a mild transient syndrome similar to clinical sepsis (Granowitz et al., 1993, J Immunol, 151 1637-1645; Lynn et al., 2003, J Infect Dis, 187 631-639). In PBMC from 8 donors, 1 μg/ml Cpn10 mediated an average 23.7% reduction, and 10 ug/ml an average 23.3% reduction in LPS-induced TNF-α secretion (FIG. 3A), illustrating that Cpn10 also reduces LPS-induced TNF-α secretion from PBMC. No significant reduction in TNF-α secretion was observed when 0.1 μg/ml of Cpn10 was used (data not shown). To illustrate that tolerance induction was not operating in this system, PBMC were pretreated with a range of LPS concentrations and 1 h later they were stimulated with 0.04 ng/ml LPS for 20 h. LPS pretreatment for 1 h did not inhibit TNF-α secretion stimulated by the second LPS treatment (FIG. 3B) illustrating that LPS tolerance does not account for the activity of Cpn10.

Figure 3:
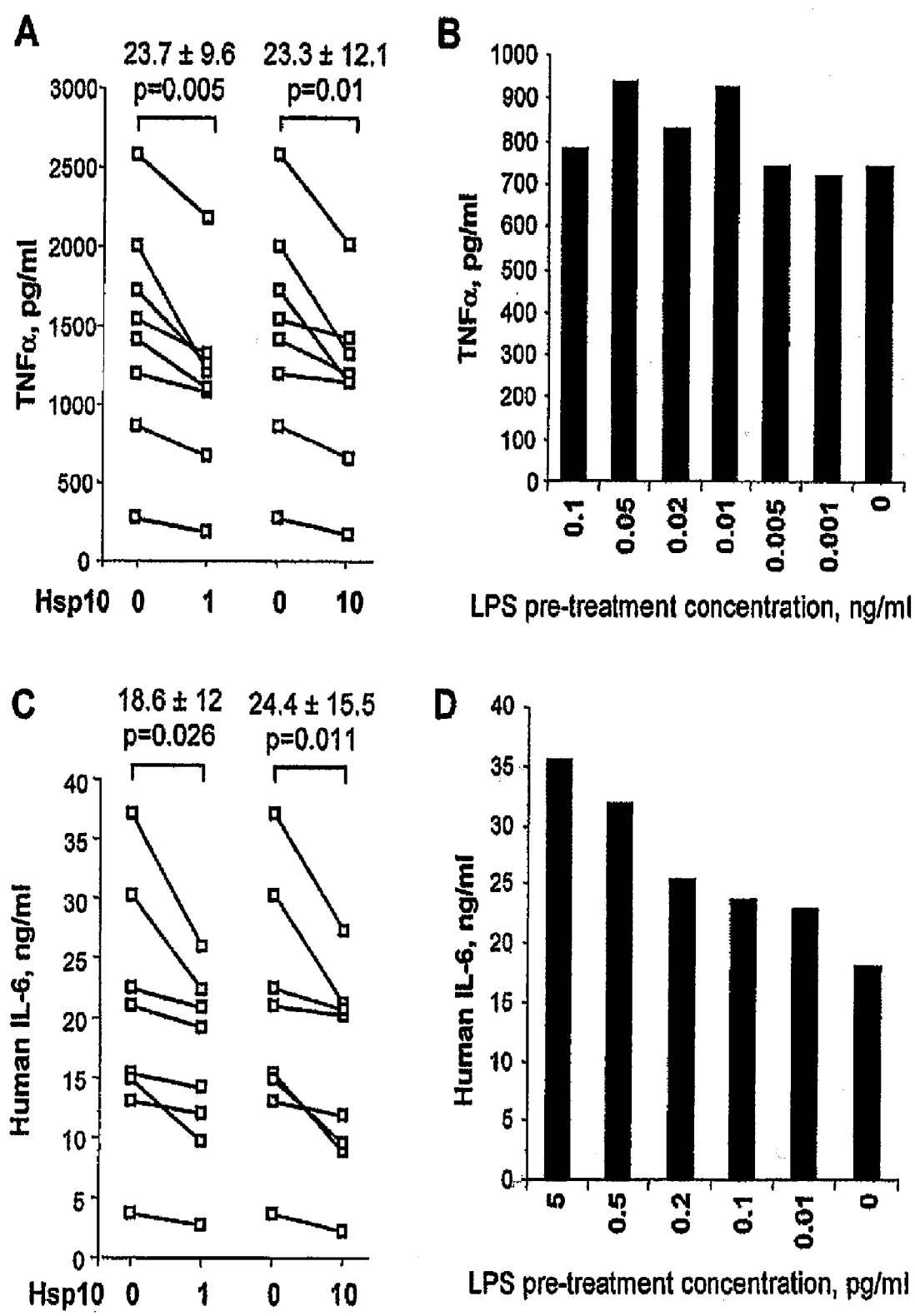
FIG. 3. Cpn10-treatment of human peripheral blood mononuclear cells (PBMC) reduces LPS-induced TNF-α and IL-6 secretion, and does not induce tolerance. (A) Cpn10 reduced LPS-induced TNF-α secretion. Cpn10 (1 and 10 μg/ml) or buffer (0) was added to PBMC from eight different donors 1 h prior to the addition of 0.04 ng/ml of LPS. Supernatants were removed after 20 h and analysed for TNF-α. The percentage reductions and significance calculated using a paired t test are indicated. For all donors 10 μg/ml of Cpn10, in the absence of LPS, failed to induce TNF-α levels above the level of detection (31 pg/ml) (data not shown). (B) Pre-treatment with LPS for 1 h was unable to induce tolerance to subsequent LPS-induced TNF-α secretion. PBMC were exposed to the indicated LPS pre-treatment concentrations. After 1 h the PBMC were stimulated with 0.04 ng/ml of LPS, and the supernatants analysed for cytokine 20 h later. (C) Cpn10 reduced LPS-induced IL-6 secretion. Cpn10 (1 and 10 μg/ml) or buffer (0) was added to PBMC from eight different donors 1 h prior to the addition of 0.04 ng/ml of LPS. Supernatants were removed after 20 h and analyzed for IL-6. The percentage reductions and significance (calculated as for A) are indicated. For all donors 10 μg/ml of Cpn10, in the absence of LPS, failed to induce IL-6 levels above the level of detection (9 pg/ml) (data not shown). (D) Pre-treatment with LPS for 1 h was unable to induce tolerance to subsequent LPS-induced IL-6 secretion. PBMC were exposed to the indicated LPS pre-treatment concentrations. After 1 h the PBMC were stimulated with 0.04 ng/ml of LPS, and the supernatants analyzed for cytokine 20 h later.

IL-6 is another well known inflammatory cytokine induced by LPS. To determine whether Cpn10 inhibited LPS-induced IL-6 secretion, PBMC from eight donors were treated with 1 or 10 μg/ml Cpn10 or buffer for 1 h followed by stimulation with 0.04 ng/ml LPS for 20 h. An average 18.6 and 24.4% reduction in LPS-induced IL-6 secretion was observed for 1 or 10 μg/ml Cpn10, respectively (FIG. 3C). No significant reduction in IL-6 secretion was observed when 0.1 μg/ml of Cpn10 was used (data not shown). LPS pretreatment for 1 h did not inhibit IL-6 secretion stimulated by a second LPS treatment, again illustrating that tolerance induction was not operating in this system (FIG. 3D)

Cpn10-treatment Inhibited LPS-induced TNF-α Secretion In Vivo

Figure 4:
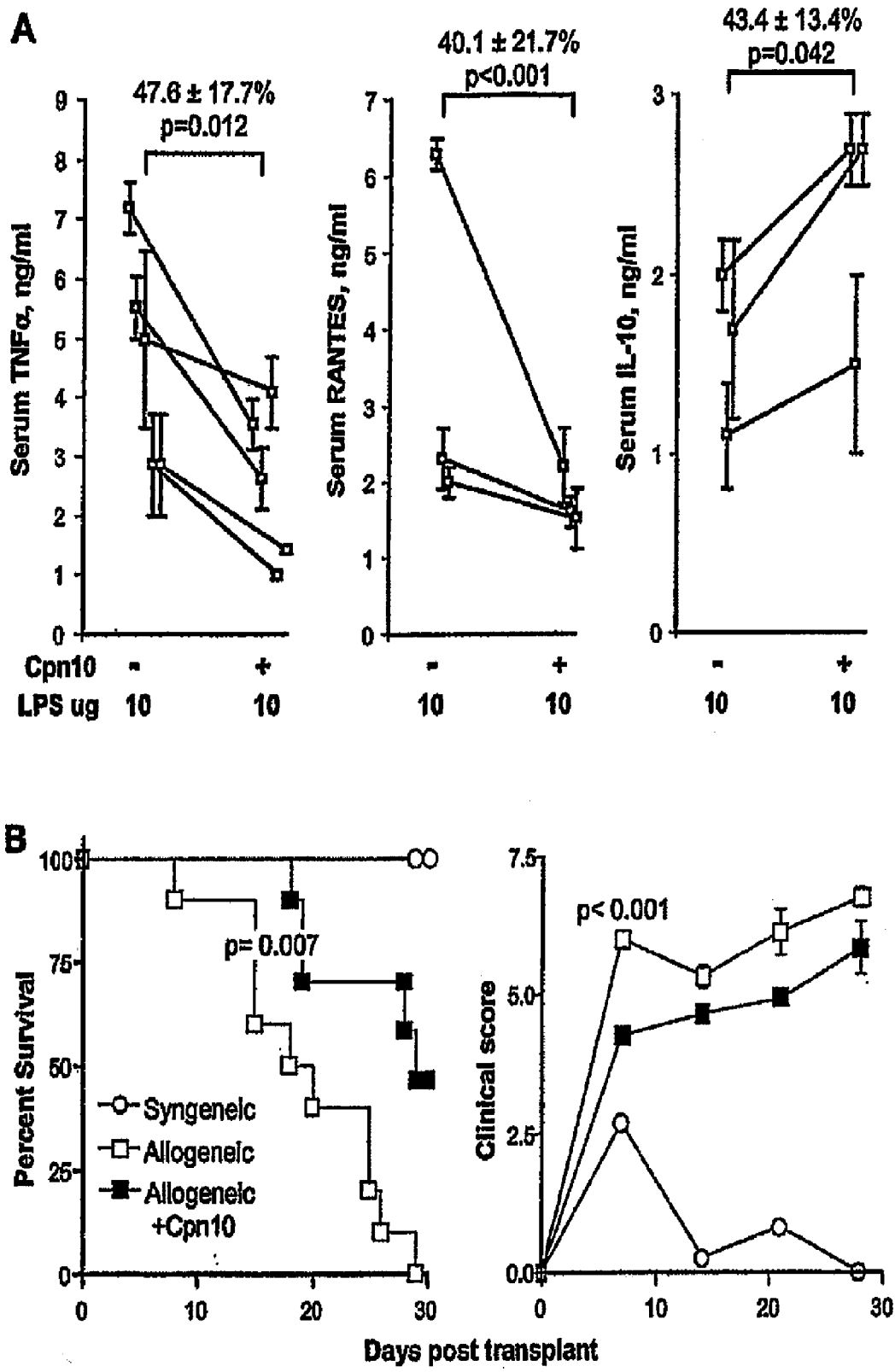
FIG. 4. Cpn10 activity in murine inflammatory models. (A) Cpn10 reduces LPS-induced serum TNF-α and RANTES levels and increases IL-10 levels. In 5 separate experiments C57BL/6 mice (n=3 or 4 per group) were given buffer (Cpn10−) or 100 μg of Cpn10 (Cpn10+) iv 30 mins before iv administration of 10 μg of LPS. After 1.5 hours the animals were sacrificed and serum TNF-α, RANTES and IL-10 levels determined; (the latter two were assessed in ⅗ experiments). Error bars represent standard errors within each experiment. The percentage reduction in TNF-α and RANTES and increase in IL-10 (±SD) is indicated and the significance calculated using ANOVA tests. (B) Pre-transplant treatment with Cpn10 delays GVHD mortality and reduces clinical severity of acute disease. Syngeneic negative controls (n=8) (white circles) represent B6D2F1 mice transplanted with syngeneic B6D2F1 bone marrow and T cells. Allogeneic positive controls (n=10) (white squares) represent diluent pre-treated B6D2F1 recipient mice transplanted with cells from diluent pre-treated B6 donor mice. Allogeneic+Cpn10 (n=10) (black squares) represent B6D2F1 recipients receiving bone marrow and T cell grafts from B6 donor mice where both recipients and donors were pre-treated with Cpn10 prior to transplantation. Kaplan-Meier survival curves and clinical scores are shown for the three groups and the allogeneic groups treated with and without Cpn10 compared by Log Rank Statistic and non-parametric t test, respectively. Clinical scores were only significantly different on day 7.

A modified endotoxemia model was used to determine whether Cpn10 delivered in vivo was able to inhibit LPS-induced TNF-α secretion in vivo. BALB/c mice were given 100 μg of Cpn10 iv 30 mins before injection of 10 μg of LPS i.v., and blood removed after 1.5 hours. Cpn10 treatment resulted in an average 47.6% reduction in the serum TNF-α, an average 40.1% reduction in serum RANTES, and an average 43.3% increase in serum IL-10 levels in several repeat experiments (FIG. 4A). Five days of daily Cpn10 pretreatment failed significantly to enhance this level of TNF-α inhibition (data not shown). These data are consistent with the previous tissue culture experiments and illustrate the in vivo efficacy of Cpn10 in reducing TNF-α and increased IL-10 production after challenge with LPS.

Cpn10 Reduced the Acute Symptoms of Graft Versus Host Disease (GIIHD)

Acute GVHD following allogeneic bone marrow transplantation (BMT) is a T cell-mediated disease in which donor T cells recognize recipient allo-antigens and differentiate in a Th1 dominant fashion. The resulting T cell-derived Th1-cytokines (primarily IFN-γ) prime the donor mononuclear cells to release cytopathic quantities of inflammatory cytokines (e.g., TNF-α) when they are stimulated with LPS that has leaked through the radiation-damaged gastrointestinal mucosa. These cytokines and the allo-reactive T cells then contribute to increasing gastrointestinal damage and LPS leakage. GVHD mortality in BMT models is prevented if the donor mononuclear cells lack TLR4, LPS is effectively blocked (by therapeutic antagonists) (Cooke et al., 2001, J Clin Invest, 107 1581-1589), or TNF-α itself is neutralized. The ability of Cpn10 administration during the peri-transplant period to ameliorate GVHD was therefore investigated. Cpn10 treatment of transplant donors and recipients prior to transplant significantly delayed GVHD mortality (FIG. 4B). In addition, the severity of GVHD as determined by clinical score was also reduced early after BMT (FIG. 4B). Although Cpn10 was able to delay GVHD and reduce early morbidity, ultimately the animals succumbed to GVHD, consistent with the inability of Cpn10 to abolish TNF-α secretion or to effect T cell proliferation and IFN$_\gamma$ secretion (data not shown). Treatment of animals with Cpn10 post transplant failed to affect significantly GVHD (data not shown).

Discussion

Cpn10 mediated a 23-56% inhibition of TNF-α secretion depending on the system used and the dose of LPS and Cpn10. Cpn10 increased LPS-induced IL-10 secretion by approximately 40-200% depending on the system, but the inhibition of TNF-α secretion was not dependent on the elevation of IL-10 production.

Since *E. coli*-derived LPS is a well-described agonist for TLR4, the experiments indicate that Cpn10 modulates TLR4 signaling through the NF-κB pathway. However, it is likely that Cpn10 modulates cytokine secretion via other pathways stimulated by the TLR4 and TLR2 complex.

The inhibitory effects of Cpn10 are mediated very rapidly, within 30 mins (FIG. 4A) to 2 hours (FIG. 1A). This implicates inhibition of early signaling events or activation of rapid negative feedback mechanisms like PI3K, rather than late phase feedback mechanisms involving IRAK or SOCS (Fukao & Koyasu, 2003, Trends Immunol, 24 358-363).

The specific PI3K inhibitor, wortmannin, had no detectable effect on Cpn10 activity (data not shown), suggesting Cpn10 does not affect the PI3K pathway.

Example 2

Cpn10 and TLR2

Materials and Methods

BALB/c mice were injected subcutaneously with ovalbumin (10 µg) (Sigma) emulsified in CFA (Sigma). CFA contains mycobacterial cell wall extracts, which are believed to contain lipopeptide agonists of TLR2 (Lim et al., 2003, Int Immunopharmacol, 3 115-118; Tsuji et al., 2000, Infect Immun; 68 6883-6890; Kirschning & Schumann, 2002, Curr Top Microbiol Immunol, 270 121-44). CFA is well known to induce granulomas (Bergeron et al., 2001, Eur Respir J, 18 357-361; Shah et al. 2001, J Assoc Physicians India, 49 366-368).

Cpn10 (100 µg) was given twice daily for 5 days with two doses preceding injection of the CFA. Subcutaneous granulomas were measured at the indicated times.

Results

Figure 5:
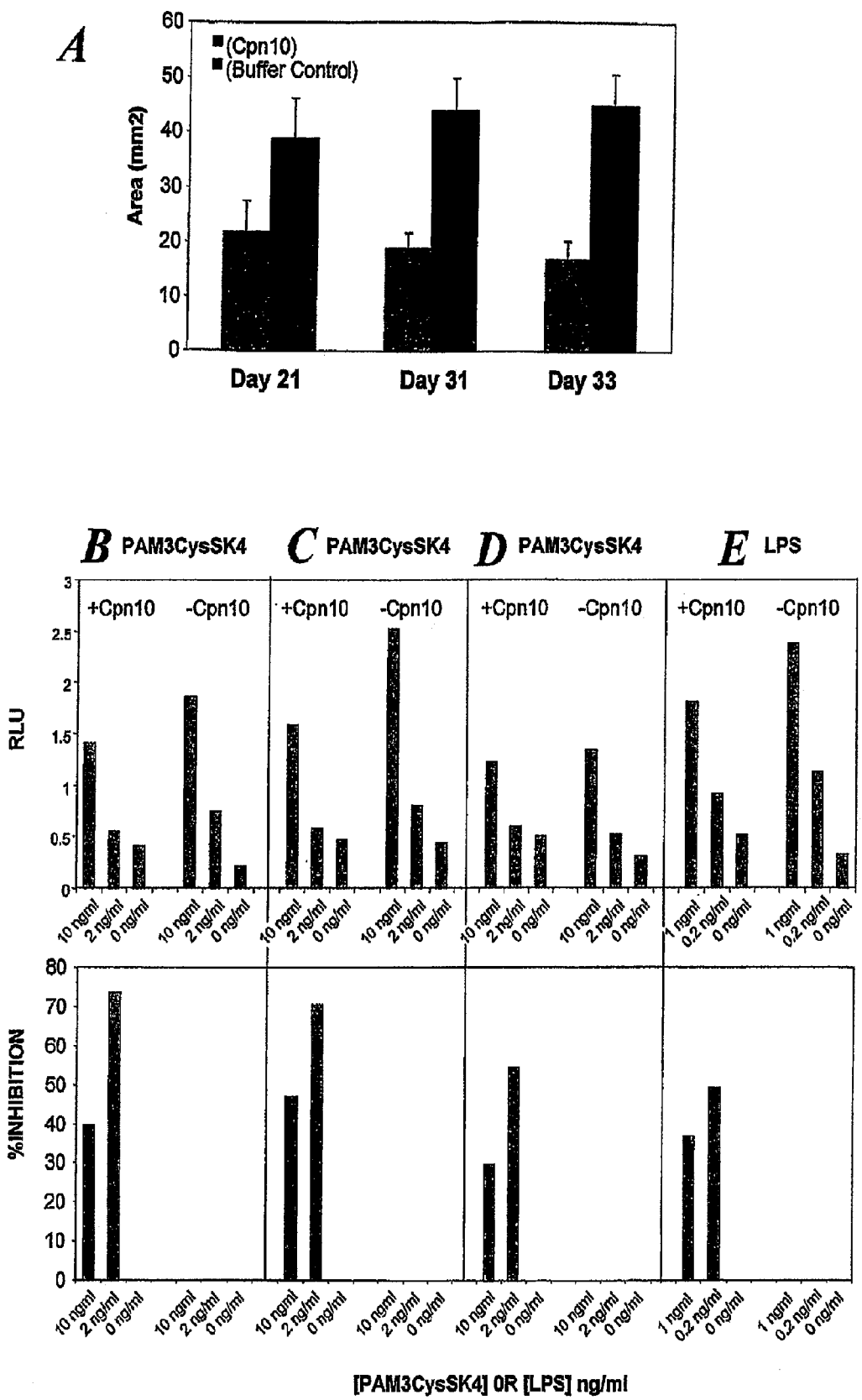
FIG. 5. (A) Area of subcutaneous granuloma present in BALB/c mice given Complete Freund's Adjuvant (CFA) with and without Cpn10 treatment. Cpn10 results are indicated by lighter-shaded columns on left of each pair of columns compared to buffer control (darker-shaded, right columns). (B-E) PAM$_3$CysSK$_4$-induced macrophage activation is inhibited by Cpn10 in RAW264-HIV-LTR-LUC cells. (B) Cpn10 or diluent added for 2 hrs followed by addition of PAM$_3$CysSK$_4$ for 2 h followed by the luciferase assay. (C) Cpn10 or diluent added for 2 hrs, followed by washing to remove Cpn10 or diluent, followed by addition of PAM$_3$CysSK$_4$ for 2 h and then the luciferase assay. (D) Cpn10 or diluent added for 2 hrs followed by addition of PAM$_3$CysSK$_4$ for 2 h and then the luciferase assay. (E) The same protocol was used as in (B) except the cells were activated with LPS instead of PAM$_3$CysSK$_4$. The top panel shows the relative light unit data, and the bottom the percent inhibition mediated by Cpn10.

To determine whether Cpn10 is able to impact CFA's granuloma formation activity, Cpn10-treated and buffer control-treated mice were injected with CFA. Cpn10 treatment significantly reduced the size of the granuloma induction (FIG. 5A).

Conclusion

As CFA stimulates TLR2, and CFA induces granuloma formation, a reduction in granuloma formation mediated by Cpn10 treatment provides evidence that Cpn10 also inhibits TLR2 signaling.

Example 3

Cpn10 Inhibits Activation of NF-κB by the TLR2 Agonist PAM$_3$CYS-SK$_4$

PAM$_3$CysSK$_4$ (a lipopeptide) is a known agonist of TLR2 (Agrawal et al., J Immunol, 2003, 171 4984-9) and is able to stimulate the HIV LTR (FIG. 5B-D), which is thought to activate transcription factors, such as NF-κB (Lee et al., J Immunol. 2002, 168 4012-4017).

Material and Methods

PAM$_3$CysSK$_4$ was purchased from EMC Microcollection GmbH and dissolved as a working stock dilution of 1 mg/ml in water. Cpn10 and the RAW264-HIV-LTR-LUC assay system was performed as described previously for LPS. Briefly RAW-LUC cells were seeded at 2.5×10$^5$ cell/ml into 24 well plates and incubated overnight at 37° C. Cpn10 was added to the cells at 120 µg/ml and incubated for 2 h at 37° C. PAM$_3$Cys-SK$_4$ (10 ng/ml or 2 ng/ml or 0 ng/ml) was then added for 2 h prior to the luciferase assay. LPS at 1 ng/ml or 0.2 ng/ml was used as a positive control.

Results

Cpn10 inhibited HIV LTR activation by the TLR2 agonist PAM$_3$CysSK$_4$ (FIG. 5B). This inhibition was maintained irrespective of whether the medium was changed before addition of Cpn10 (FIG. 5C) or before addition of PAM$_3$CysSK$_4$ (FIG. 5D).

Conclusion

Cpn10 is able to inhibit pro-inflammatory mediator activation signals in macrophages stimulated by a TLR2 agonist.

Example 4

Immunoprecipitation of Cpn10 with Toll-like Receptor in the Presence of Ligand

Materials and Methods

Immunoprecipitation

TLR4 was provided as a fusion of TLR4 extracellular domain (ECD) with mouse Fc heavy chain (T4:Fc) in conditioned medium from secreting cells (10 ml/point). T4:Fc was collected by centrifugation using 20 µl packed protein A beads (PAS, CL4B, Sigma) and the pellet washed 3× with lysis buffer before separation by SDS-PAGE. Proteins were electrotransferred onto Hybond-C nitrocellulose membranes. Membranes were blocked in 5% dry milk in PBS and 0.1% Tween 20 for 30 min at 37° C. and probed for an additional 30 min at 37° C. with HRP conjugated anti-mouse antibody (Visintin et al., 2003, J. Biol. Chem. 278 48313-48320.)

For binding, 1 µg baculoviral MD-2 or 10 µg Cpn10 were added to the T4:Fc/PAS mix and incubated overnight at 4° C. TLR2 was used as a control bait. In addition, 10 µg Cpn10 was immunoprecipitated using 2 µg of anti-Cpn10 polyclonal antibody. As a control, no Cpn10 was added to the IP (to detect non-specific background banding of antibody). Both MD-2 (1 µg) and Cpn10 (10 µg) were loaded in a lane to show total amount loaded (INPUT).

Results

A co-immunoprecipitation experiment was performed to determine whether recombinant Cpn10 interacts directly with recombinant TLR2: or TLR4:Fc fusion proteins. Recombinant MD-2 was used as a control (which interacts with TLR4 but not TLR2).

Figure 6:
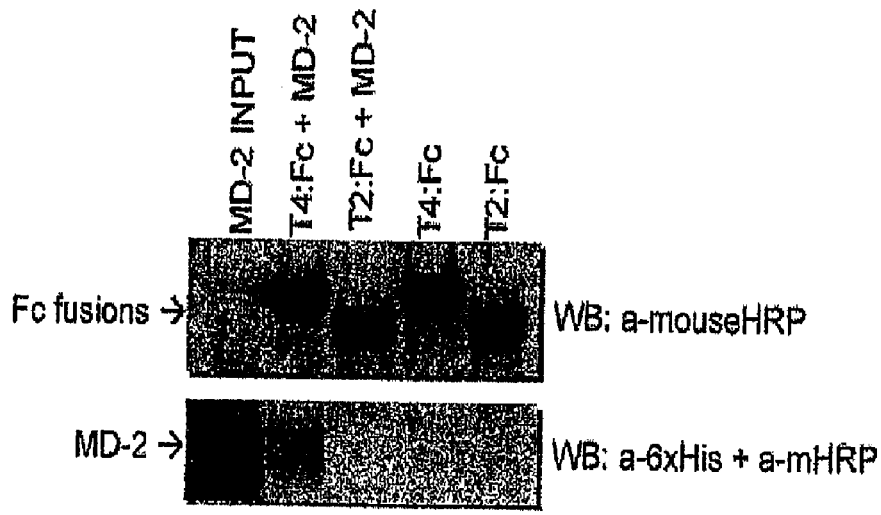
FIG. 6. Cpn10 does not bind TLR4 or TLR2 in the absence of ligand. Upper panel: TLR4 positive control. MD-2 co-immunoprecipitates with TLR4 (but not with TLR2). Lower Panel: Cpn10 does not physically interact with either TLR4 or TLR2 under these conditions and in the absence of ligand.
Figure 6:
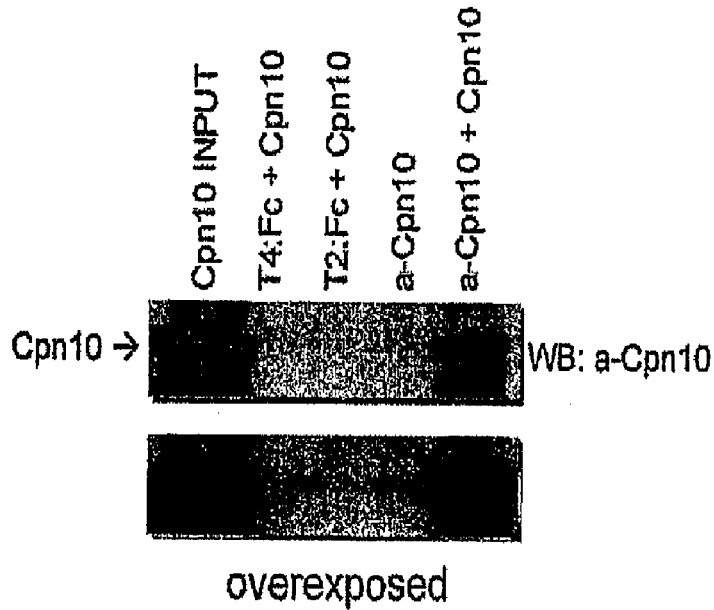

FIG. 6 (top panel) demonstrates that MD-2 co-immunoprecipitates with TLR4 (but not with TLR2). The bottom panel of FIG. 6 shows that Cpn10 does not physically interact with either TLR4 or TLR2 in the absence of ligand.

Example 5

FRET Analysis of Cpn10 Interaction with Toll-like Receptor in the Presence of Ligand Introduction The plasma membrane of cells is composed of lateral heterogeneities, patches and microdomains. These membrane microdomains or lipid rafts are enriched in glycosphingolipids and cholesterol and have been implicated in cellular processes such as membrane sorting and signal transduction. The importance of lipid raft formation in the innate immune recognition of bacteria has been investigated using biochemical and fluorescence imaging techniques. It was found that receptor molecules that are implicated in LPS-cellular activation, including CD14, Hsp70, Hsp90, chemokine receptor 4 (CXCR4), growth differentiation factor 5 (GDF5) and TLR4 are present in microdomains following LPS stimulation. Lipid raft integrity is essential for LPS-cellular activation, since raft-disrupting drugs, such as nystatin or MCD, inhibit LPS-induced TNF-α secretion. These results suggest that the entire bacterial recognition system is based around the ligation of CD14 by bacterial components and the recruitment of multiple signalling molecules, such as Hsp70, Hsp90, CXCR4, GDF5 and TLR4, at the site of CD14-LPS ligation, within the lipid rafts (Triantafilou et al., 2002, J Cell Sci 115 2603).

Cpn10 dose-dependently reduces the signal intensity of LPS-stimulation of human and mouse cells, both in vivo and in vitro. It was therefore proposed that Cpn10 may localize to the lipid raft during LPS signal clustering, by binding either directly to TLR4 or to one of the other participants of the cluster to disrupt signaling.

The results presented herein represent data obtained from FRET assays using Cpn10 and rabbit polyclonal anti-Cpn10 antibody.

Materials and Methods
FRET Measurements

Fluorescence resonance energy transfer (FRET) is a non-invasive imaging technique used to determine molecular proximity. FRET can occur over 1-10 nm distances and effectively increases the resolution of light microscopy to the molecular level. It involves nonradiative transfer of energy from the excited state of a donor molecule to an appropriate acceptor. The rate of energy transfer is inversely proportional to the sixth power of the distance between the donor and the acceptor.

In this FRET study, samples were labelled with donor- and acceptor-conjugated antibodies, and energy transfer was detected as an increase in donor fluorescence (dequenching) after complete photobleaching of the acceptor molecule. FRET images were calculated from the increase in donor fluorescence after acceptor photobleaching. Here, FRET was used to determine the concentration of receptor molecules involved in LPS-induced cell activation (MonoMac6 cells) in lipid rafts.

Results

By performing FRET experiments, it was possible to investigate whether Cpn10 was co-localizing with lipid rafts. FRET was measured in terms of dequenching donor fluorescence after complete photobleaching of the acceptor fluorophore. Increased donor fluorescence after destruction of the acceptor indicated that donor fluorescence was quenched in the presence of the acceptor because of energy transfer.

By testing the energy transfer efficiency using a positive control, that is, energy transfer between monoclonal antibodies to different epitopes on GM1 (ganglioside, a raft-associated molecule) molecules, it was shown that the maximum energy transfer efficiency (E %) was 37±1.0.

A negative control between FITC-GM1 and rhodamine-MHC was also used, which revealed no significant energy transfer (3±0.4). This background FRET value is thought to be caused by random FRET as both species are present at high concentrations.

Data presented in Table 1 demonstrate that CD14 resides in lipid rafts, as described in a recent publication (Triantafilou et al., J Cell Science 2002, supra), but that TLR4 and Cpn10 were not found to be associated with lipid rafts prior to LPS stimulation, and are apparently recruited there after LPS stimulation.

The data in Table 2 describe the proximity of Cpn10 to the TLR4 cluster, again using FRET. In Table 2, the positive control was TLR4 with itself, and gave a maximum energy transfer efficiency (E %) of 36±2.0.

As shown in Table 2, Cpn10 did not associate with Hsp70, Hsp90 or CXCR4 in absence of LPS, but demonstrated an association with these members of the LPS-activation cluster after LPS stimulation. While the data demonstrating whether there is an association of Cpn10 with TLR4 prior to LPS stimulation is not shown here, there is a strong association of Cpn10 with TLR4 upon LPS stimulation.

Example 6

Cpn10 and Cachexia

Materials and Methods
Induction of Adjuvant-induced Cachexia

The aim of the present study was to determine whether Cpn10 administration to rats during development of adjuvant arthritis would result in decreased weight loss. Female Dark Agouti rats (n=30, 150-160 g) were injected subcutaneously with 0.1 ml of CFA at the base of the tail. The adjuvant consisted of incomplete Freund's adjuvant (Difco, Michigan, USA) to which was added 10 mg/ml heat-killed *Mycobacterium tuberculosis* H37RA (Difco). The onset of detectable arthritic disease in this model is generally 8-10 days after CFA injection.

Cpn10 Treatment

Rats were injected subcutaneously with 0.25 mg/kg (n=10) or 2.5 mg/kg Cpn10 (n=10) or diluent control (Tris/saline buffer) (n=10) daily from day-2 to day 13, and weighed on a daily basis.

Statistical Analysis

The difference in weight observed in rats receiving Cpn10 or diluent control were tested for significance using univariate analysis of variance (ANOVA).

Results

Figure 7:
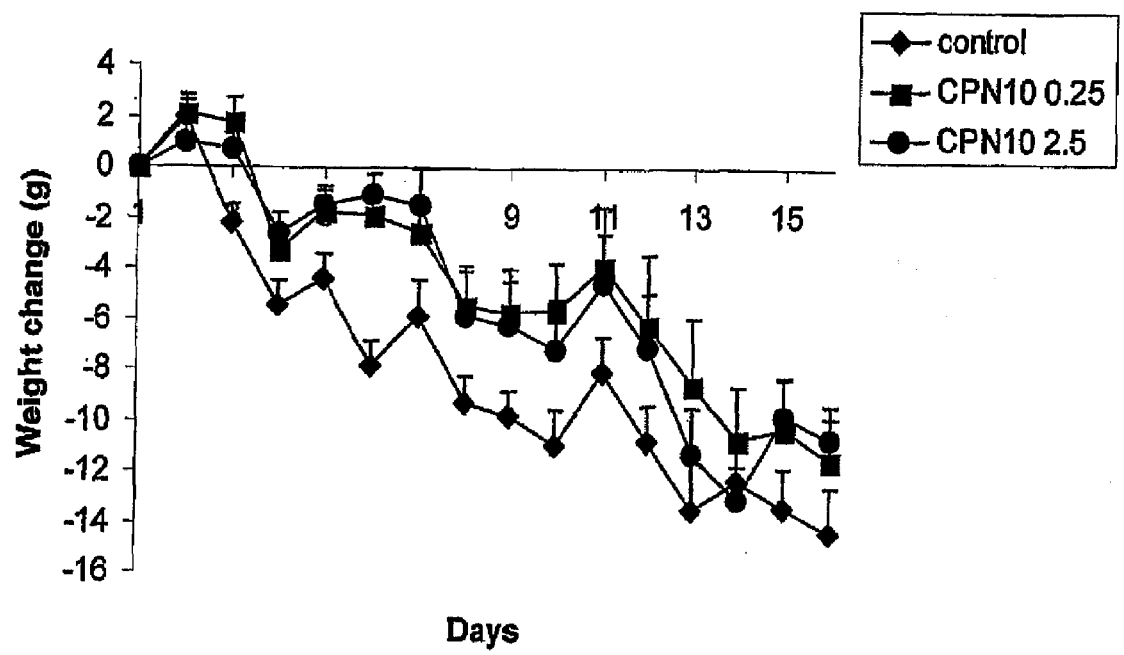
FIG. 7. Daily subcutaneous administration of Cpn10 reduces weight loss during adjuvant arthritis in rats. Mean (±SEM) weight loss during adjuvant arthritis (n=10 per group).

There was a net loss of weight in all groups following administration of CFA, which appeared more marked in the control group (FIG. 7).

When the weight loss data for the 0.25 and 2.5 mg/kg Cpn10 treatment groups were pooled and compared with the control group, there was a statistically significant difference p=0.027) in weight loss. The pooling of data from the two treatment groups is justified in this case due to the similar values of weight loss in the two groups (p=0.94) over this time period.

Conclusion

Adjuvant arthritis leads to changes in body composition and cytokine production that mimics pro-inflammatory cytokine-driven cachexia in chronic inflammatory arthritis (Mayer, 1997, Arthritis Rheum, 40 534-539). Cpn10 administration in vivo or in vitro reduces production of pro-inflammatory cytokines by cells stimulated by LPS and other agonists.

The effects of Cpn10 were tested at two doses in rats in which cachexia was induced experimentally with a single injection of CFA. Diluent control and Cpn10 were administered subcutaneously to animals of similar weight and age. The administration of CFA resulted in a significant decrease in body weight. By comparing the Cpn10 treated versus control treated groups, there was a statistically significant reduction in weight loss in the Cpn10-treated rats.

Elevated levels of inflammatory cytokines including TNF-α, IL-1β and IL-6 are known to correlate with cachexia in a number of diseases, including cancer and rheumatoid arthritis (Argiles, 2003. Curr Opin Clin Nutr Metab Care, 6 401-406; Walsmith, 2002, Int J Cardiol, 85 89-99). We have shown that administration of Cpn10 reduces production of TNF-α, IL-6 and RANTES, and increases production of the anti-inflammatory cytokine IL-10 in murine models of endotoxemia and graft-versus-host-disease, and in vitro LPS-stimulation of freshly isolated PBMC and monocyte cell lines.

Example 7

Cpn10 does not Induce Tolerance

Materials and Methods
RAW264-HIV-LTR-LUC Bioassay
RAW264-HIV-LTR-LUC cells were cultured and plated for assay as described above. The cells were incubated with LPS, Cpn10 or control buffers for 2 h, followed by the addition of stimulating LPS at the indicated concentrations. After a further 2 h incubation, the adherent cells were processed for the luciferase assay (Luciferase Assay System, Promega, Madison, Wis.). Luciferase activity was read for 15 sec on a Turner Designs Luminometer TD 20/20.
Production and Purification of Cpn10
Recombinant human Cpn10 was produced and purified as described above.
Trypsin Treatment of Cpn10
2.5% trypsin (Gibco) was filtered through an Acrodisc as above twice and added at 40 µg/ml to Cpn10 (at 2-3 mg/ml). After incubation at 37° C. overnight the trypsin/Cpn10 solution was heated to 90° C. for 15 mins to destroy trypsin activity prior to addition to the bioassays. After trypsin treatment no Cpn10 could be detected by SDS-PAGE and Western blotting, and the material was inactive in the rhodenese refolding assay (data not shown).
Statistical Analysis
Statistical analysis (univariate analysis of variance-ANOVA, Student's t test or log rank statistic) was performed using SPSS for Windows 11.5.0 (SPSS Inc.).
Results
Tolerance Induction was Not Responsible for Inhibition of LPS Signaling in RAW264-HIV -LTR-LUC Cells
LPS tolerance is a well-recognized phenomenon whereby the response to a second stimulus with LPS is reduced. LPS tolerance is normally induced if the time interval between the two LPS exposures exceeds 3 h and the concentration of the LPS during the initial exposure is sufficiently high to stimulate the macrophages (West & Heagy, 2002, Crit. Care Med 30 S64-S73; Fujihara et al., 2003, Pharmacol. Ther. 100 171-194).

Figure 8:
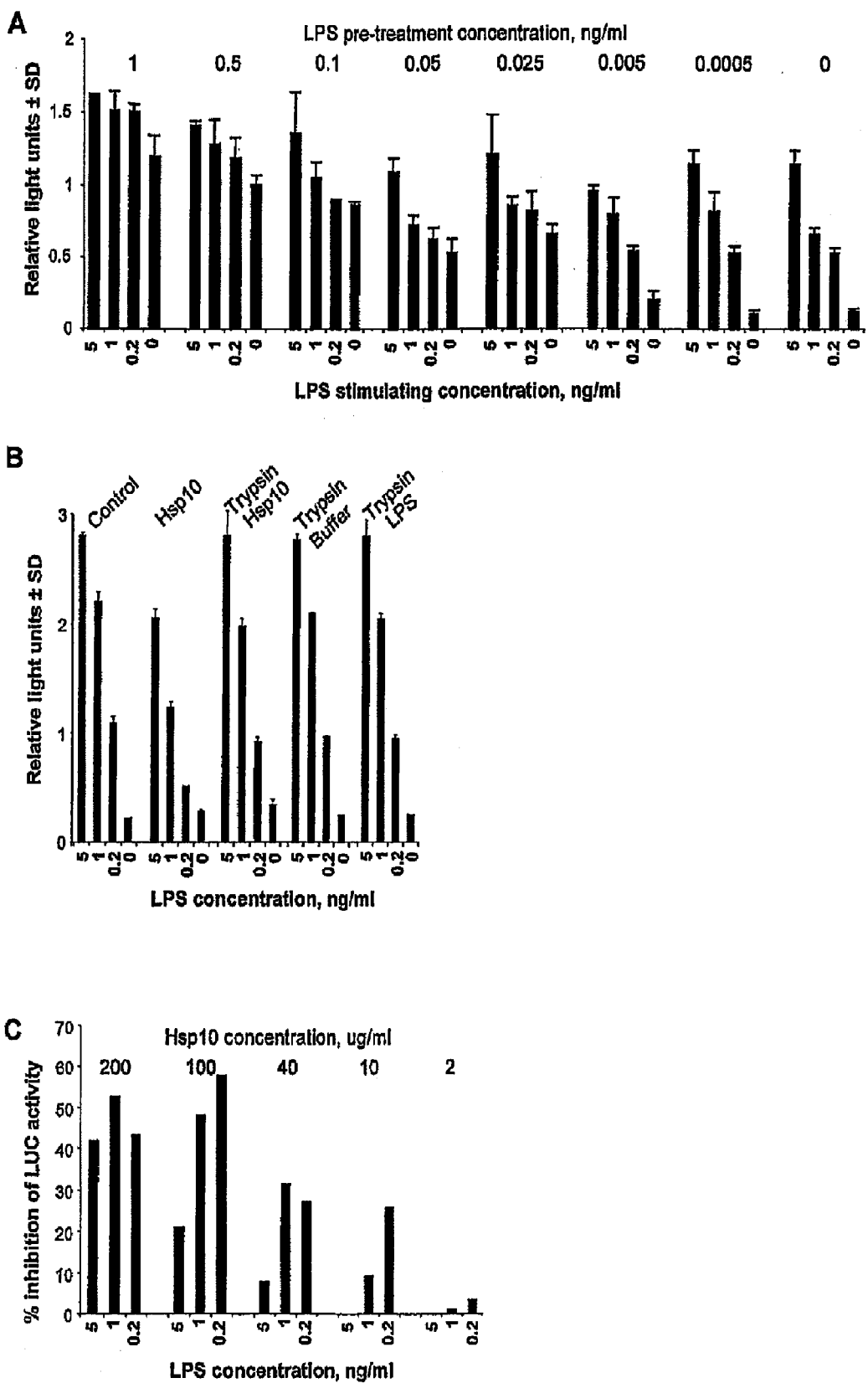
FIG. 8. Cpn10-mediated activity on LPS-stimulated RAW264.7 cells is not due to contamination with LPS (A) As a test for tolerance due to LPS contamination of Cpn10, it was shown that LPS pre-treatment 2 h prior to LPS stimulation did not inhibit LUC activity. RAW264-HUV-LTR-LUC cells were pre-treated with the indicated LPS concentrations in duplicate; after 2 h the cells were stimulated with 5, 1, 0.2 and 0 ng/ml LPS and the LUC activity measured 2 h later. (B) Trypsin-treated Cpn10 failed to inhibit LPS-induced NF-κB activity. Treatment of RAW264-HIV-LTR-LUC cells in duplicate for 2 h with 100 μg/ml Cpn10 (Hsp10) significantly reduced the RLU induced by 5, 1 and 0.2 ng/ml LPS compared with cells treated with buffer (Control); percent reductions in RLU after subtraction of background were 29.7±0.8 (SD), 50±4.6, and 71±7.7, respectively (p<0.001 by two factor ANOVA, which included a term for LPS concentration). Compared with the Control, treatment with trypsin-treated Cpn10 (Trypsin Hsp 10) gave 0.1±8.8, 11.6±4.2, and 21±7.4, and trypsin-treated buffer (Trypsin Buffer) 1.4±2.1, 5.8±1.1, and 14.9±2.4 percent reduction for 5, 1 and 0.2 ng/ml LPS, respectively; (neither were significantly different from Control or each other). As expected, trypsin treatment of the stimulating LPS did not affect LPS activity (Trypsin LPS, p>0.05). (C) Cpn10-mediated reduction in LPS-induced LUC activity is dose responsive. The experiment was set up as in FIG. 1A except the Cpn10 (Hsp10) concentration was varied as indicated. For each LPS concentration the percent inhibition in LUC activity over control cells not pre-treated with Cpn10 is indicated.

To formally discount tolerance induction as being responsible for the observations in FIG. 1A, RAW264-HIV-LTR-LUC cells were pre-treated with a range of LPS concentrations for 2 h followed by stimulation with 5, 1 and 0.2 ng/ml LPS. Pre-treatment with LPS concentrations ranging from 1 to 0.0005 ng/ml did not inhibit the induction of LUC activity by the second LPS exposure (FIG. 8A). Thus for the RAW264-HIV-LTR-LUC system the 2 h pre-treatment period appeared insufficient for tolerance induction. Furthermore, sub-stimulating doses (0.005-0.0005 ng/ml), potentially similar to those found in Cpn10 preparations, also failed to inhibit LPS-mediated LUC activity. LPS tolerance was therefore unlikely to be responsible for the observations in FIG. 1A since (i) the 2 h interval between LPS exposures was insufficient for LPS tolerance induction in the RAW-264-HIV-LTR -LUC system, and (ii) undetectable (or sub-stimulating) levels of LPS, which are potentially contaminating the Cpn10 preparations, were unable to mediate LPS tolerance.
Cpn10 is Sensitive to Trypsin-digestion
To illustrate that the inhibitory activity of Cpn10 (FIG. 1A) was lost following proteolytic degradation, Cpn10 was digested with trypsin and the trypsin activity destroyed by heating before addition to the bioassays. Destruction of Cpn10 by trypsin was confirmed by SDS-PAGE/Western blotting and the rhodanese refolding assay (data not shown). (Heating alone failed to affect significantly Cpn10 activity in the LUC or the rhodanese refolding assays-data not shown). Cpn10 pretreatment again significantly inhibited LPS-mediated luciferase activity (FIG. 8B, Control versus Hsp10, $p<0.001$, see figure legend). However, trypsin/heat-treatment Cpn10 failed to inhibit LPS signaling (FIG. 8B, Trypsin Hsp10), giving values similar to trypsin/heat-treated buffer controls (FIG. 8B, Trypsin Buffer). As expected, trypsin treatment (followed by heating at 90° C. for 15 mins) failed to affect significantly the activity of *E. coli* LPS (FIG. 8B, Trypsin LPS). Thus proteolytic degradation of Cpn10 resulted in the loss of inhibitory activity by Cpn10 preparations, illustrating that trypsin-resistant contaminants (e.g., LPS) of the Cpn10 preparations were not responsible for the inhibitory activity.
Cpn10-mediated Reduction of LPS-stimulated LUC Activity in RAW264 Cells was Dose Responsive
The percent reductions in LUC activity shown in FIG. 1A were obtained using 100 µg/ml of Cpn10. To determine whether the activity of Cpn10 was dose responsive, RAW264-HIV-LTR-LUC cells were treated with a range of Cpn10 concentrations prior to the addition of LPS. (Treatment with 100 µg/ml thus represents a repeat of the experiments shown in FIG. 1A). A clear dose response emerged with increasing levels of inhibition apparent from 2 to 100 µg of Cpn10, with the inhibitory appearing to level off after 100 µg/ml (FIG. 8C).

Example 8

Effect of Cpn10 in Human Clinical Trial Subjects

Phase Ia Clinical Trial
Materials and Methods
Nineteen healthy normal volunteers aged between 18 and 55 years were enrolled in a 14-day phase I trial of Cpn10 to assess the pharmacokinetics and safety of Cpn10 administered as a single intravenous infusion or subcutaneous injection in a double-blind placebo control protocol. Following screening and written informed consent, subjects were fasted overnight prior to dosing with Cpn10 at 1, 2.5, 5 or 10 mg given as a 10 minute intravenous infusion, or 5 mg given subcutaneously. Blood samples (50 ml) for PBMC isolation were collected prior to dose (approximately 12 hours pre-dose), 8 hours post-dose, and on day 6 following Cpn10 dose. Subjects were monitored for 14 days post treatment for adverse events, with blood drawn at intervals for standard haematology and biochemistry assessment and development of anti-Cpn10 antibodies.

PBMC Isolation and Storage

PBMC were isolated from heparinized blood by density gradient centrifugation on Ficoll-Hypaque Plus (Amersham) using the manufacturer's protocol. Following two wash steps, cells were resuspended in freezing medium (10% DMSO in fetal bovine serum [FBS]) and frozen using a step-down freezing method at −70° C. Cells were transported on dry ice and then stored in liquid nitrogen until use.

PBMC Stimulation

PBMC were thawed and centrifuged through FBS followed by washing and resuspending in RPMI with 10% FBS. Cells were aliquoted at a final density of $1 \times 10^6$ viable cells/ml in 24-well tissue culture plates with or without LPS. Following 20 hrs incubation at 37° C. with 5% $CO_2$, cell culture supernates were collected and tested for levels of TNF-α using a commercial human TNF-α ELISA (R&D Systems).

Results

Figure 9A:
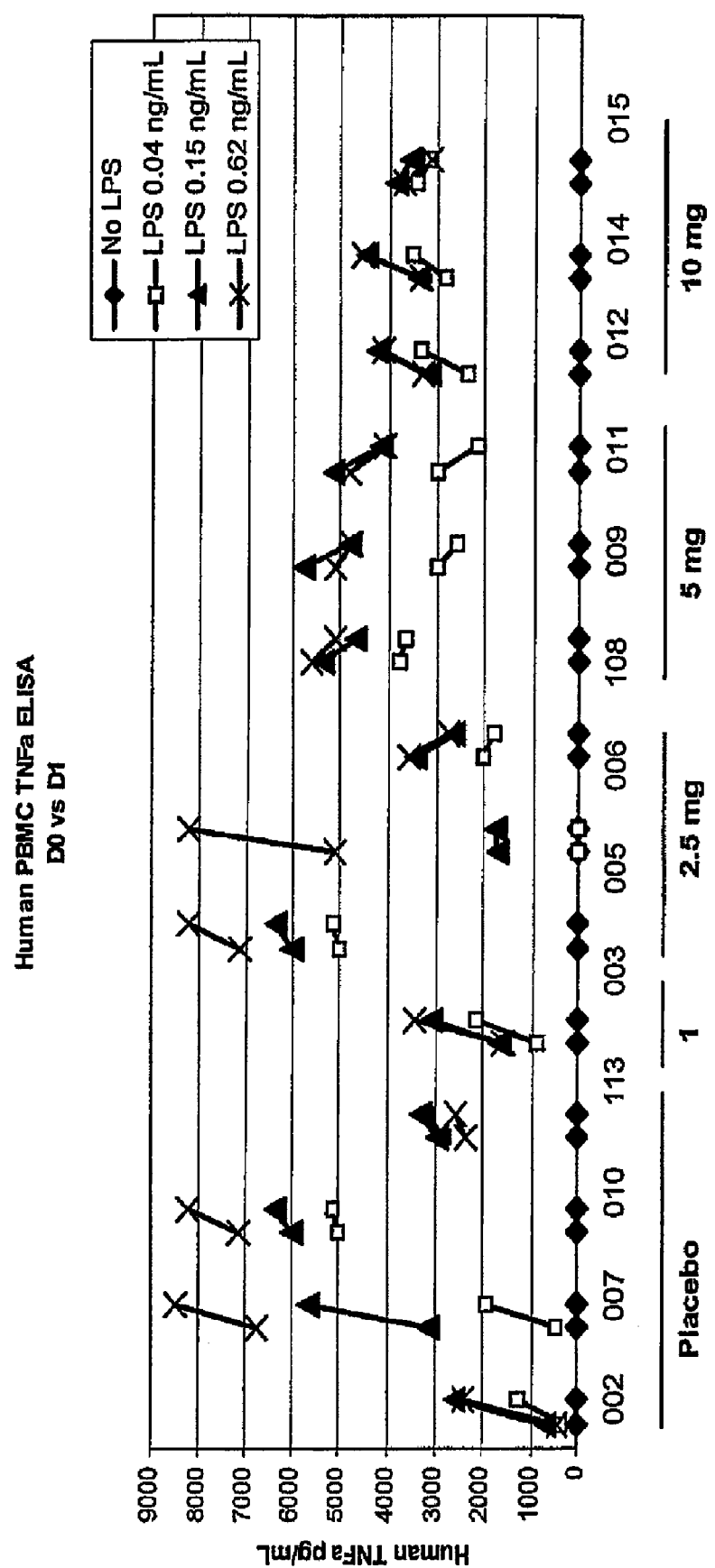
FIG. 9. Intravenous infusion, but not subcutaneous injection, of Cpn10 induces changes in the magnitude of the LPS-driven TNF-α response by PBMC in vitro. (A) LPS-driven TNF-α production on day 0 (~12 hr pre-infusion) and day 1 (8 hr post-infusion). (B) Data from FIG. 9A graphed as the change in LPS-driven TNF-α production from pre- to post-infusion. (C) LPS-stimulated TNF-α production on day 0 (~12 hr pre-injection) vs. day 1 (8 hr post-subcutaneous injection Cpn10/placebo).
Figure 9B:
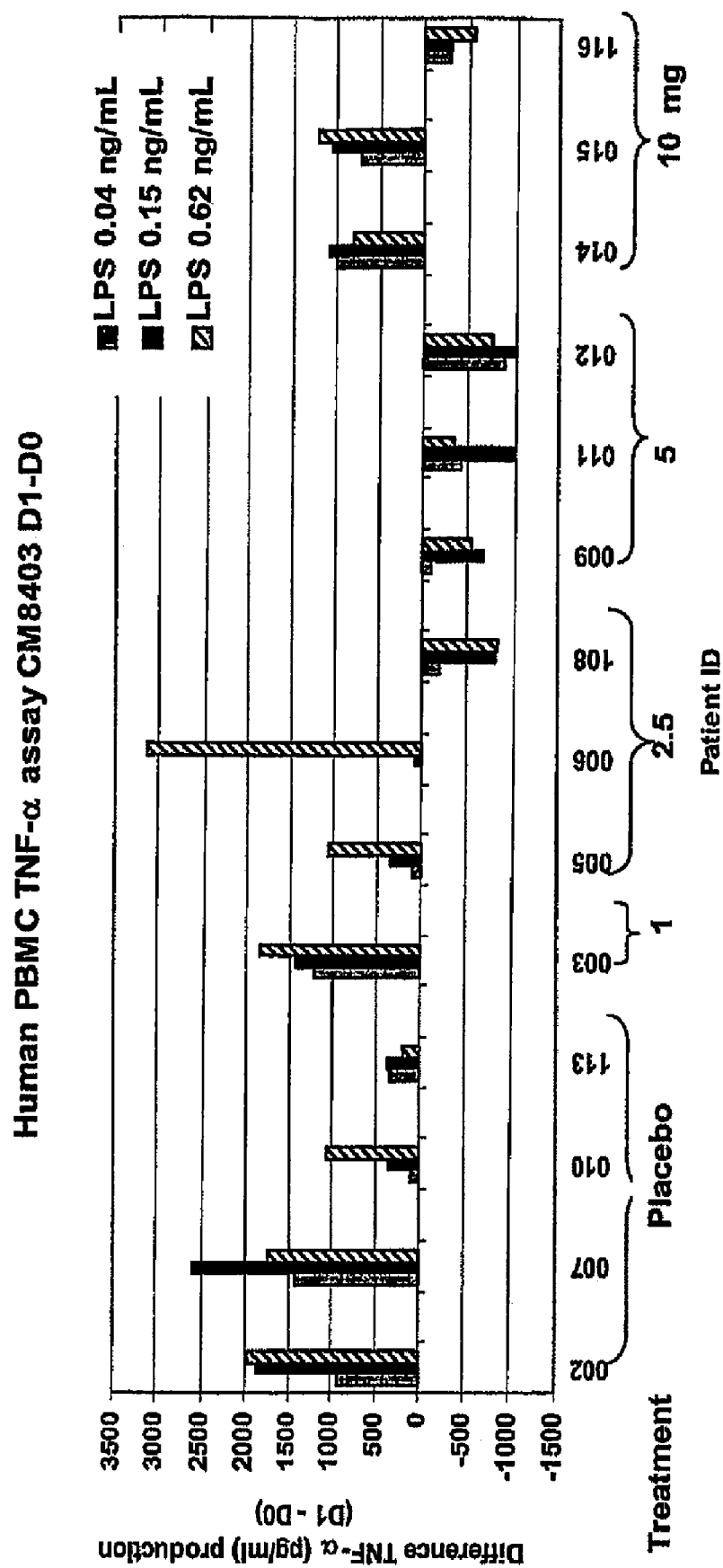
Figure 9C:
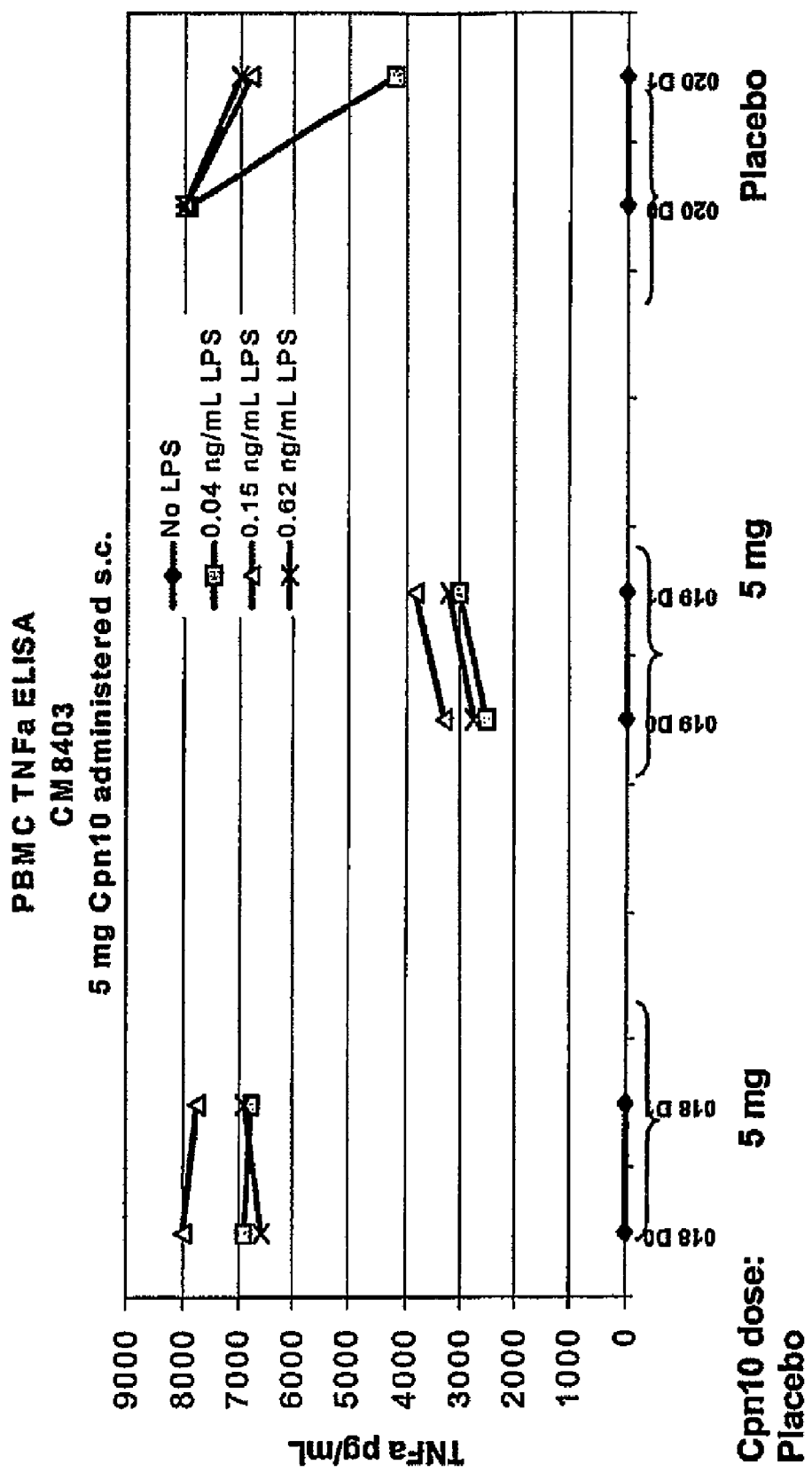

We have compared the LPS-driven response at day 1 vs. day 0 (i.e., post-Cpn10 vs. pre-Cpn10) in groups of volunteers given 1 mg (n=1), 2.5 mg (n=3), 5 mg (n=3), and 10 mg Cpn10 (n=3) or placebo (n=3). (Note: PBMC from subjects 001 and 004 (1 mg Cpn10 cohort) were not viable due to haemolysis of blood samples. Therefore, data from PBMC for this cohort includes only one subject.) FIGS. 9A and 9B demonstrate a dose-responsive Cpn10-mediated change in TNF-α production by PBMC stimulated with a range of LPS concentrations in vitro. That is, the LPS-driven response at day 1 relative to day 0 was reduced in 1 out of 3 subjects in the 2.5 mg cohort, in 3 out of 3 subjects in the 5 mg cohort, and in 1 out of 3 subjects in the 10 mg cohort. While inconclusive due to the small cohort size, the data seem to indicate a slight reversal of the trend seen in the 5 mg group, when the dose was increased to 10 mg. In subjects given 5 mg Cpn10 via subcutaneous injection, there does not appear to be a Cpn10-mediated effect on TNF-α production (FIG. 9C), however the cohort size is again too small to provide conclusive data.

Conclusions

As a predictor of a Cpn10-mediated change in immune activity during a phase I clinical trial, we collected peripheral blood mononuclear cells (PBMC) approximately 12 hours before, and 8 hours after a single intravenous infusion or subcutaneous injection of Cpn10 (or placebo). These cells were stimulated with a range of LPS concentrations in vitro in the absence of exogenous Cpn10 to assess the level of TNF-α production. The data suggest there may be an effect of Cpn10 in reducing the pro-inflammatory response, when administered in the dose range of 2.5 to 10 mg. However, the cohorts in this study were very small and more data will be accumulated to support a hypothesis about Cpn10's biological effect in vivo. Data from the 10 mg dose cohort seem to be inconsistent with the trend in TNF-α response from the groups given 2.5 and 5 mg Cpn10, although the small cohort size prohibits any analysis of these data beyond speculation.

The lack of an effect in this in vitro assay from PBMC isolated from subjects given 5 mg Cpn10 subcutaneously is most likely related to the relatively small amount of protein that is detectable (and thus bioavailable) in the circulation by ELISA.

We note that PBMC were isolated at a time-point (8 hrs post-dose) at which we could no longer measure Cpn10 in the serum (data not shown), supporting a view that while the $t_{1/2}$ of this recombinant protein is short (~1 hr), its biological effects may be longer-lived. It is also important to point out that the change (i.e., increase) in the LPS response on day 1 vs. day 0 (e.g., in placebo subjects) is a well-documented phenomenon in both rodents and humans, and is thought to be related to the stress response (Granowitz et al., 1993. J Immunol 151 1637). That is, the increased LPS-driven response by PBMC on day 1 vs. day 0 may be due to the stress of the trial, i.e., administration an untested drug, multiple blood draws, etc. Cpn10 (a member of the stress protein group) may be involved in reducing the stress-related exacerbation in the inflammatory response.

Phase Ib Clinical Trial

Materials and Methods

Ten volunteers aged between 18 and 65 years with multiple sclerosis not currently receiving immunomodulatory treatment were enrolled in a 28-day phase Ib trial to assess the safety, tolerability and pharmacokinetics of Cpn10 administered as multiple intravenous infusions. This was a placebo-controlled double blind multiple dose escalation study. Similar to the design of the Phase Ia, subjects were dosed with Cpn10 (or placebo) at 5 or 10 mg in an intravenous infusion. Blood samples for PBMC isolation were collected approximately 12 hours pre-dose and 8 hours post-dose on days 1 and 5. To assess the longevity of the biological effect of Cpn10, blood was drawn for PBMC isolation at 3 and 7 days following the last infusion of the compound (at day 5).

PBMC were isolated, stored and stimulated as described for the Phase Ia clinical trial.

Results

Figure 10:
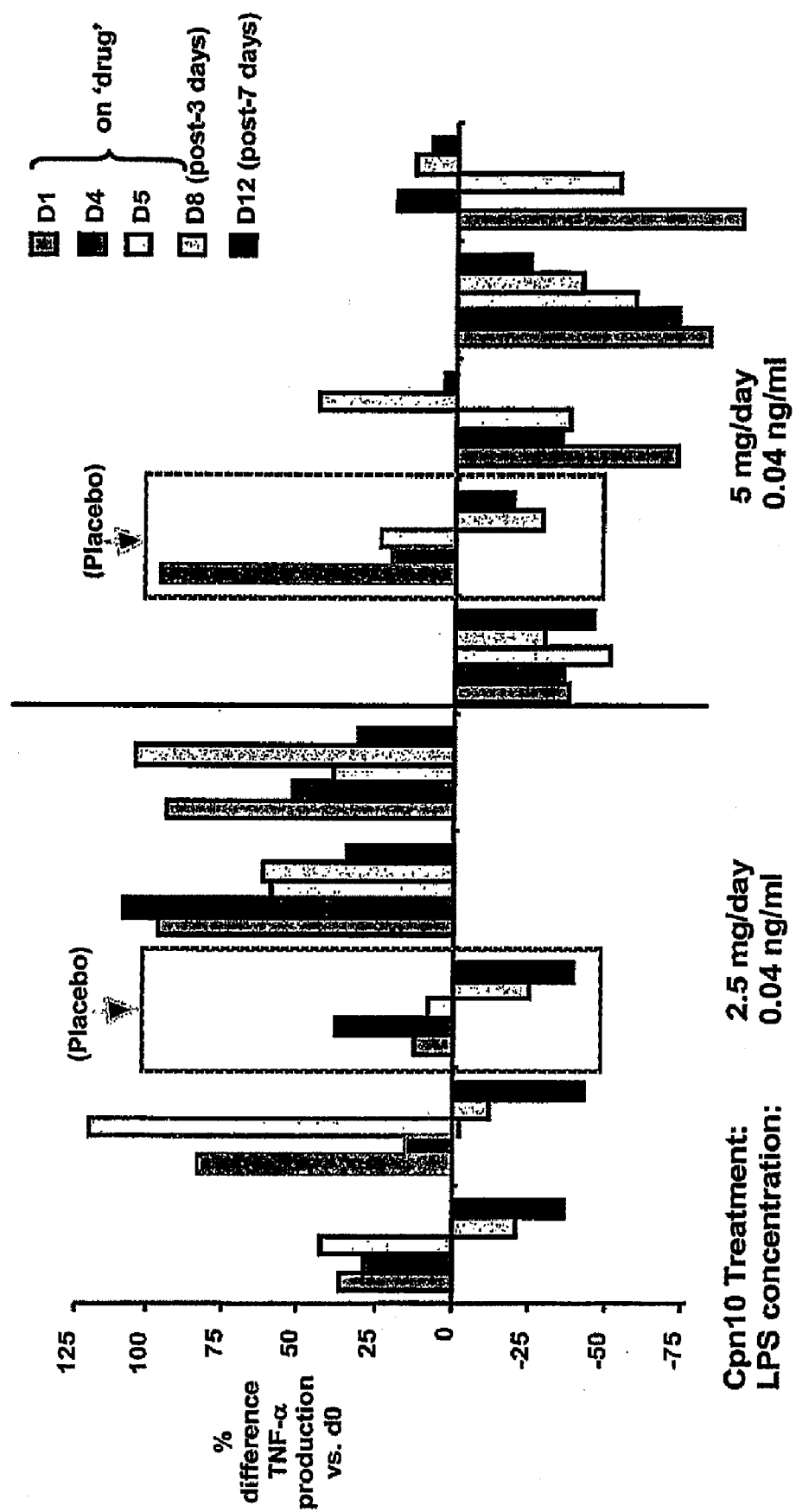
FIG. 10. Intravenous infusion of Cpn10, daily for 5 days, induces changes in the magnitude of the LPS-driven TNF-α response by PBMC in vitro. LPS-driven TNF-α production from PBMC isolated on day 0 (~12 hr pre-infusion) compared with cells isolated on days 1, 4, and 5 (approx. 8 hr post-infusion). In addition, PBMC isolated on days 8 and 12 (i.e., 3 days and 7 days following the final day 5 Cpn10 infusion, respectively) were compared with the day 0 LPS-stimulated response. Cell culture supernatants were also tested for production of IL-6 and demonstrated the same overall trend as depicted here for TNF-α.

We have compared the LPS-driven response at days 1, 4, 5, 8, and 12 vs. day 0 (i.e., post-Cpn10 vs. pre-Cpn01) in groups of volunteers given 5 daily intravenous infusions of 2.5 (n=4) or 5 mg Cpn10 (n=4) or placebo (n=2). FIG. 10 demonstrates a dose-responsive Cpn10-mediated change in TNF-α production by PBMC stimulated with LPS in vitro. Note that data are described as the percent difference in TNF-α produced in response to LPS stimulation at D1 relative to D0, and at D4 relative to D0, etc. That is, the LPS-driven response at D1 relative to D0 was reduced in all 4 subjects in the 5 mg Cpn10-treated cohort by 38-94%. Comparing the D4 values to the D0 TNF-α values within this cohort, the percent reduction in TNF-α production was 36-72%, and 38-59% when comparing the D5 to D0 TNF-α production. There was no reduction in LPS-stimulated TNF-α in the 2.5 mg Cpn10 treatment group at any time-point while 'on drug', i.e., at days 1, 4, and 5 during the trial.

Conclusion

As a predictor of a Cpn10-mediated change in immune activity during a Phase Ib clinical trial in volunteers with multiple sclerosis, we collected peripheral blood mononuclear cells (PBMC) approximately 12 hours before, and about 8 hours after intravenous infusion of Cpn10 (or placebo) on days 1, 4 and 5 during a five-day daily infusion protocol. In addition, PBMC were isolated on days 3 and 7 following the final infusion of Cpn10. These cells were stimulated with LPS in vitro in the absence of exogenous Cpn10 to assess the level of TNF-α production. The data suggest there may be an effect of Cpn10 in reducing the pro-inflammatory response, when administered at 5 mg/day. That is, in all four subjects in Cohort B given 5 mg/day Cpn10, there was a marked reduction in LPS-stimulated TNF-α on days 1, 4 and 5. By contrast, in subjects given 2.5 mg/day Cpn10, there was no noted reduction in LPS-induced TNF-α production while 'on drug', i.e., on days 1, 4, and 5. There was also no reduction in LPS-stimulated TNF-α production in cells from the two subjects infused with placebo (Cpn10 vehicle). However, the two cohorts in this study were very small and more data will be accumulated to support a hypothesis about Cpn10's biological effect in vivo.

As in the Phase Ia trial, we note that PBMC were isolated at a time-point (8 hrs post-dose) at which we could no longer measure Cpn10 in the serum, supporting a view that while the $t_{1/2}$ of this recombinant protein is short (~1 hr), its biological effects may be longer-lived. However, from these few data points it is impossible to ascribe a longer-lasting effect of Cpn10 on inflammatory cytokine production than 12 hours.

As also noted during the Phase Ia trial, it is also important to point out that the change (i.e., increase) in the LPS response on day 1 vs. day 0 (e.g., in placebo subjects) is a well-documented phenomenon in both rodents and humans, and is thought to be related to the stress response (Granowitz et al., 1993, supra).

TNF-α production by cells isolated on days 8 and 12 from placebo subjects, as well as some subjects given Cpn10, may be related to the fact that subjects were out-patients at these time-points and therefore may have been less nervous or stressed. As previously suggested, Cpn10 (a member of the stress protein group) may be involved in reducing the stress-related exacerbation in the inflammatory response.

SUMMARY

In addition to its critical role in protein folding within the mitochondria, Cpn10 appears to have an extracellular role in the modulation of specific inflammatory processes. In a number of different human and murine in vitro systems and in two murine disease models, Cpn10 consistently inhibited LPS-induced secretion of the pro-inflammatory cytokines TNF-α and IL-6 and/or the pro-inflammatory chemokine RANTES, and increased LPS-induced secretion of the anti-inflammatory cytokine IL-10. The Cpn10-mediated reduction in TNF-α secretion was never absolute; instead Cpn10 mediated an approximate 25-60% reduction in TNF-α levels, depending on the system and the dose of LPS and Cpn10. Cpn10 increased LPS-induced IL-10 secretion by approximately 40-200% depending on the system, but the reduction in TNF-α secretion was not dependent on this elevation of IL-10.

Given that *E. coli*-derived LPS is a well-described agonist for TLR4, the experiments described herein indicate that Cpn10 can down-modulate TLR4 signaling. How exactly Cpn10 mediates its inhibitory activity is unclear although it appears to effect inhibition very rapidly, within 30 mins (FIG. 4A) to 2 h (FIG. 1A). This might implicate inhibition of early signaling events or activation of rapid negative feedback mechanisms such as phosphoinositide 3-kinase (PI3K). However, we have been unable to prevent Cpn10 activity with the specific PI3K inhibitor, wortmannin, suggesting this pathway is not involved in the Cpn10 mechanism of action.

The ability to reduce, but not suppress completely, TNF-α secretion would distinguish Cpn10 from other anti-inflammatory therapies, particularly those based on anti-TNF-α antibodies, which can accomplish efficient removal of TNF-α. However, such removal may not always be desirable. For instance, TNF-α antibody treatment has been shown ultimately to increase the severity of multiple sclerosis (MS; Wiendl & Hohlfeld, 2002, BioDrugs 16, 183-200). MS has been suggested as a possible therapeutic target for Cpn10 since Cpn10 is reported to reduce clinical signs and delay onset of disease in a murine model of MS (experimental autoimmune encephalomyelitis; Zhang et al., 2003, J Neurol Sci 212: 37-46).

As described herein, the ability of Cpn10 to reduce the expression of inflammatory mediators indicates that Cpn10 may find therapeutic application in conditions where excessive LPS, TLR4, and/or TLR2 signaling leads to pathology.

Furthermore, this mode of action is not via tolerance induction or preferential activation/suppression of Th1/Th2 responses.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein are incorporated herein by reference.

TABLE 1

Energy transfer efficiency values between donor-acceptor pairs.

| Donor (Cy3) | Acceptor (Cy5) | E ± ΔE (%) |
|---|---|---|
| Unstimulated MM6 cells | | |
| GM1 | GM1 | 37 ± 1.0 |
| GM1 | MHC class I | 3 ± 0.4 |
| GM1 | CD14 | 34 ± 2.0 |
| GM1 | TLR4 | 5 ± 1.5 |
| GM1 | Cpn10 | 15 ± 2.0 |
| MM6 cells stimulated with LPS | | |
| GM1 | MHC class I | 3 ± 0.5 |
| GM1 | CD14 | 35 ± 1.5 |
| GM1 | TLR4 | 32 ± 1.8 |
| GM1 | Cpn10 | 28 ± 2.0 |

Energy transfer between different pairs was detected from the increase in donor fluorescence after acceptor photobleaching. Data represent mean±standard deviation of a number of independent experiments.

TABLE 2

Energy transfer efficiency values between donor-acceptor pairs.

| Donor (Cy3) | Acceptor (Cy5) | E ± ΔE (%) |
|---|---|---|
| Unstimulated MM6 cells | | |
| TLR4 | TLR4 | 36 ± 2.0 |
| Cpn10 | CD14 | 12 ± 0.5 |
| Cpn10 | Hsp70 | 9 ± 1.0 |
| Cpn10 | Hsp90 | 6 ± 2.0 |
| Cpn10 | CXCR4 | 3 ± 1.0 |
| MM6 cells stimulated with LPS | | |
| Cpn10 | TLR4 | 36 |
| Cpn10 | CD14 | 32 ± 0.5 |
| Cpn10 | Hsp70 | 24 ± 1.0 |
| Cpn10 | Hsp90 | 18 ± 12.0 |
| Cpn10 | CXCR4 | 12 ± 1.0 |

Energy transfer between different pairs was detected from the increase in donor fluorescence after acceptor photobleaching. Data represent mean±standard deviation of a number of independent experiments.

What is claimed is:

1. A method of screening for a Chaperonin 10 (Cpn10) antagonist comprising the steps of:

forming a molecular complex comprising a Toll-like receptor, a Toll-like receptor agonist and Cpn10 in the presence and absence of a candidate Cpn10 antagonist; and detecting whether formation of the molecular complex is prevented or disrupted by the presence of the candidate Cpn10 antagonist;

wherein a candidate Cpn10 antagonist detected to prevent or disrupt formation of the molecular complex is identified as a Cpn10 antagonist.

2. The method of claim 1, wherein the Toll-like receptor is selected from the group consisting of TLR2 and TLR4.

* * * * *